(12) United States Patent
Nakahara et al.

(10) Patent No.: US 8,822,212 B2
(45) Date of Patent: Sep. 2, 2014

(54) METHODS FOR FORMING TOOTH ROOT AND PERIODONTAL TISSUE UNIT, AND REGENERATED TOOTH

(75) Inventors: Taka Nakahara, Chiyoda-ku (JP); Hiroshi Ishikawa, Chiyoda-ku (JP); Soh Sato, Chiyoda-ku (JP); Masato Ohta, Chiba (JP)

(73) Assignee: The Nippon Dental University, Tokyo (JP)

( * ) Notice: Subject to any disclaimer, the term of this patent is extended or adjusted under 35 U.S.C. 154(b) by 818 days.

(21) Appl. No.: 13/040,672

(22) Filed: Mar. 4, 2011

(65) Prior Publication Data

US 2011/0212418 A1     Sep. 1, 2011

Related U.S. Application Data

(63) Continuation of application No. PCT/JP2009/065388, filed on Sep. 3, 2009.

(30) Foreign Application Priority Data

Sep. 5, 2008    (JP) .................................. 2008-228858

(51) Int. Cl.
| | |
|---|---|
| *C12N 5/00* | (2006.01) |
| *A61C 13/00* | (2006.01) |
| *A61L 27/36* | (2006.01) |
| *A61L 27/38* | (2006.01) |

(52) U.S. Cl.
CPC ......... *A61L 27/3604* (2013.01); *A61L 27/3865* (2013.01); *A61L 27/3804* (2013.01)
USPC ........... 435/325; 435/377; 435/404; 435/405; 435/406; 433/167; 424/93.1

(58) Field of Classification Search
CPC combination set(s) only.
See application file for complete search history.

(56) References Cited

U.S. PATENT DOCUMENTS

| 8,349,608 B2 * | 1/2013 | Tsuji et al. .................... 435/377 |
| 2005/0069570 A1 | 3/2005 | Ishibashi et al. |

FOREIGN PATENT DOCUMENTS

| JP | 07-188053 | 7/1995 |
| WO | 2008/067488 | 6/2008 |

OTHER PUBLICATIONS

Gomez Flores et al., "Cementum-periodontal ligament complex regeneration using the cell sheet technique," Journal of Periodontal Research, vol. 43, No. 3, 2008, pp. 364-371.
Nakao et al., "FGF-2 potently induces both proliferation and DSP expression in collagen type 1 gel cultures of adult incisor immature pulp cells," Biochemical and Biophysical Research Communications, vol. 325, No. 3, 2004, pp. 1052-1059.
Tsuji, "Tooth regeneration as dental therapy for next generation," The Journal of the Japan Dental Association, 2007, vol. 60, No. 7, pp. 635-646 (English language translation provided).
Hu et al., "Tissue engineering of tooth crown, root, and periodontium," Tissue Engineering, 2006, vol. 12, No. 8, pp. 2069-2075.
Tsuji et al., "Round-table discussion: tooth regenerative therapy," The Journal of Japan Dental Association, vol. 60, No. 7, pp. 657-674 (English language translation provided).
Nakahara et al., "Tooth regeneration: implications for the use of bioengineered organs in first-wave organ replacement," Human Cell, 2007, vol. 20, pp. 63-70.
Young et al., "Tissue engineering of complex tooth structures on biodegradable polymer scaffolds," J Dent Res, 2002, vol. 81, No. 10, pp. 695-700.
Modino et al., "Tissue engineering of teeth using adult stem cells," Archives of Oral Biology, 2005, vol. 50, pp. 255-258.

* cited by examiner

*Primary Examiner* — Daniel C Gamett
(74) *Attorney, Agent, or Firm* — Hamre, Schumann, Mueller & Larson, P.C.

(57) ABSTRACT

A method for forming at least a tooth root in a tooth containing a tooth crown, including: forming a culture core containing the tooth and a cell-containing base material, the tooth being wrapped with the cell-containing base material, and culturing the culture core in a medium to form at least the tooth root in the tooth contained therein, wherein the cell-containing base material contains at least one kind of cells selected from periodontal ligament-derived cells, bone marrow-derived cells, dental follicle-derived cells, dental pulp-derived cells and dental papilla-derived cells, and the medium contains a component contained in a conditioned medium of a serum-free-cultured cell line of a human uterocervical squamous carcinoma cell line; an additive containing at least one selected from IL-1β, IL-6, IL-8, IL-9, EGF, IGF-I, GH, PDGF-AB, VEGF, LIF, HGF, FGF-2, FGF-1, BMP-2, BMP-4, M-CSF, dexamethasone, insulin, thyroxine, thyrocalcitonin, ascorbic acid and β-glycerophosphate; or both of them.

12 Claims, 26 Drawing Sheets

METHODS FOR FORMING TOOTH ROOT AND PERIODONTAL TISSUE UNIT, AND REGENERATED TOOTH

CROSS-REFERENCE TO RELATED APPLICATION

This is a continuation application of PCT/JP2009/065388, filed on Sep. 3, 2009.

BACKGROUND OF THE INVENTION

1. Field of the Invention

The present invention relates to, for example, a method for forming an organ of mammals; especially to, for example, a method for forming a mammals' tooth root, mammals' periodontal tissues (periodontium) and a complex structure (unit) thereof.

2. Description of the Related Art

Recent interest has focused on regenerative medical techniques which aim to restore the forms (morphology) and functions of organs suffering from tissue loss or functional disorders. In this technical field, demand has arisen for provision of regenerated organs replaceable with organs suffering from, for example, functional disorders. Such regenerated organs are required to have normal morphology and functions, and also to be formed by a technique involving no in vivo culturing. This is because there is any risk that organs formed through xenotransplantation or allotransplantation are associated with immune rejection and infection with viruses.

Thus, there is a need to regenerate organs through in vitro culturing, which does not involve such infection or other problems.

For example, in dental therapy where the regeneration of a tooth is desired, the following treatment is needed rather than using tooth crowns restored with prostheses by modern clinical techniques in dentistry. Specifically, it is desired to provide a tooth root having functions of, for example, fixing a tooth in the jawbone and supporting a tooth crown; and periodontal tissues (periodontal ligament, alveolar bone, cementum and gingiva) supporting the tooth root. In particular, it is desired to provide tooth roots having periodontal ligament and alveolar bone. Periodontal ligament is a soft tissue (connective tissue) embedded between the cementum and the inner wall of the alveolar bone socket. This periodontal ligament has the functions of cushioning mechanical forces and enabling sensory perception during chewing.

Young C S, Terada S, Vacanti J P, Honda M, Bartlett J D and Yelick P C disclose a technique based on in vivo culturing in "Tissue engineering of complex tooth structures on biodegradable polymer scaffolds; J. Dent. Res, 81, 695-700, 2002." Specifically, a cell suspension is prepared using various kinds of tooth germ-derived cells obtained from unerupted third molars of six-month-old pigs, and then applied to biodegradable polymer shaped into the form of tooth, whereby artificial tooth germs are formed. The thus-formed tooth germs are xenotransplanted into rat's omentum (intraperitoneal fat membrane) where abundant blood flows to supply a sufficient amount of nutrients and oxygen. It was confirmed that small tooth-like tissue such as enamel, dentin and dental pulp were formed 25 weeks to 30 weeks after transplantation.

Modino S A and Sharpe P T disclose a technique of reproducing the developmental processes of a tooth, focusing on epithelial-mesenchymal interactions in "Tissue engineering of teeth using adult stem cells; Arch. Oral Biol., 50, 255-258, 2005." According to this literature, artificial tooth germs are prepared by combining tooth germ epithelium taken from mouse embryos at embryonic day 10 with, rather than tooth germ mesenchyme, three kinds of stem cells which are not derived from tooth germs. Thereafter, the thus-prepared artificial tooth germs are allotransplanted under the kidney capsule of adult mice, and grown through in vivo culturing for 12 days to form teeth.

As described in "Young C S, Terada S, Vacanti J P, Honda M, Bartlett J D, Yelick P C, Tissue engineering of complex tooth structures on biodegradable polymer scaffolds; J. Dent. Res., 81, 695-700, 2002" and "Modino S A, Sharpe P T; Tissue engineering of teeth using adult stem cells; Arch. Oral Biol., 50, 255-258, 2005," hitherto, there are known only tooth regeneration techniques that require xenotransplantation or allotransplantation (in vivo culturing). This is because, as described in "The Journal of the Japan Dental Association, Vol. 60, No. 7, October 2007, 657-674," in vitro culture cannot form complete teeth, and also cannot form periodontal tissues due to lack of bones such as alveolar bone. Therefore, at present, it is necessary to perform xenotransplantation or allotransplantation (in vivo culture) in order to form teeth. In addition, no report has been presented on regeneration of human teeth, and clinically, metal (titanium) is used as a dental implant (artificial tooth root) to take the place of the tooth root.

BRIEF SUMMARY OF THE INVENTION

The present invention solves the above existing problems and aims to achieve the following objects. Specifically, an object of the present invention is to provide a method for forming at least a tooth root in a tooth containing a tooth crown through in vitro culturing; i.e., without using xenotransplantation or allotransplantation techniques (in vivo culturing). The other object of the present invention is to provide a regenerated tooth obtained by the above method.

The present inventors have conducted extensive studies to solve the above existing problems, and as a result have obtained the following finding. That is, the present inventors have found that a tooth root, periodontal tissues (periodontal ligament, alveolar bone, cementum and gingiva) or a complex structure thereof can be formed in a tooth containing a tooth crown by forming a culture core containing the tooth and a cell-containing base material, the tooth being wrapped with the cell-containing base material, and by culturing the culture core in a medium so as to form at least the tooth root in the tooth contained in the culture core, wherein the cell-containing base material contains at least one kind of cells selected from periodontal ligament-derived cells, bone marrow-derived cells, dental follicle-derived cells, dental pulp-derived cells and dental papilla-derived cells, and wherein the medium contains a component contained in a conditioned medium of a serum-free-cultured cell line of a human uterocervical squamous carcinoma cell line; an additive containing at least one selected from IL-1β, IL-6, IL-8, IL-9, EGF, IGF-I, GH, PDGF-AB, VEGF, LIF, HGF, FGF-2, FGF-1, BMP-2, BMP-4, M-CSF, dexamethasone, insulin, thyroxine, thyrocalcitonin, ascorbic acid and β-glycerophosphate; or both of the component and the additive. On the basis of this finding, the present invention has been accomplished.

The "tooth root and periodontal tissue unit" used in the present invention is a name clearly showing a character of containing as one complex structure (unit) a tooth root and periodontal tissues which are simultaneously formed by the method of the present invention.

The present invention is based on the finding obtained by the present inventors. Means for solving the above existing problems are as follows.

<1> A method for forming at least a tooth root in a tooth containing a tooth crown, the method including:
forming a culture core containing the tooth and a cell-containing base material, the tooth being wrapped with the cell-containing base material, and
culturing the culture core in a medium so as to form at least the tooth root in the tooth contained in the culture core,
wherein the cell-containing base material contains at least one kind of cells selected from periodontal ligament-derived cells, bone marrow-derived cells, dental follicle-derived cells, dental pulp-derived cells and dental papilla-derived cells, and
wherein the medium contains a component contained in a conditioned medium of a serum-free-cultured cell line of a human uterocervical squamous carcinoma cell line; an additive containing at least one selected from IL-1β, IL-6, IL-8, IL-9, EGF, IGF-I, GH, PDGF-AB, VEGF, LIF, HGF, FGF-2, FGF-1, BMP-2, BMP-4, M-CSF, dexamethasone, insulin, thyroxine, thyrocalcitonin, ascorbic acid and β-glycerophosphate; or both of the component and the additive.

<2> The method according to <1>, wherein the culturing further provides a formation of periodontal tissue.

<3> The method according to <1> or <2>, wherein the cell-containing base material is at least one of a cell sheet and a cell-containing porous base material.

<4> The method according to any one of <1> to <3>, wherein the culture core is wrapped with a cell-free porous base material.

<5> The method according to claim <3> or <4>, wherein the forming includes pre-culturing the tooth on the cell sheet.

<6> A regenerated tooth including:
a tooth root,
wherein the regenerated tooth is obtained by the method according to any one of claims <1> to <5>.

<7> The regenerated tooth according to claim <6> further including periodontal tissues.

The present invention can provide a method for forming at least a tooth root in a tooth containing a tooth crown through in vitro culture; i.e., without using xenotransplantation or allotransplantation (in vivo culture) and a regenerated tooth obtained by the above method. These can solve the above existing problems and achieve the above-described objects.

DETAILED DESCRIPTION OF THE INVENTION

Figure 1:
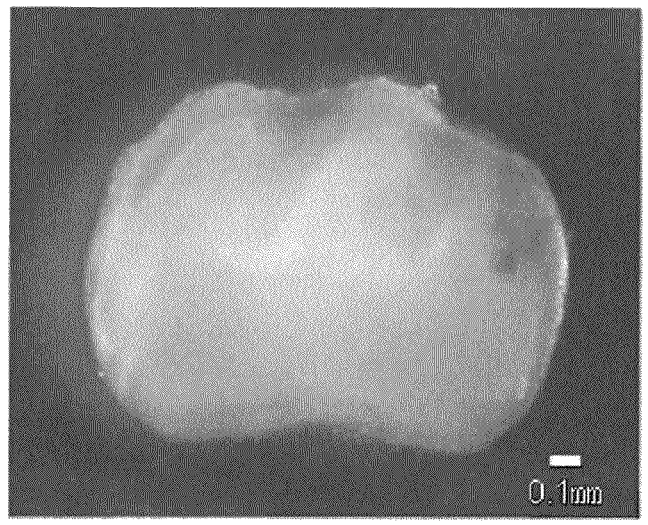
FIG. 1 is an explanatory view (stereomicroscope image) of the mouse tooth crown used in Example 1.

[Method for Forming at Least a Tooth Root of Tooth Containing a Tooth Crown]

A method of the present invention for forming at least a tooth root in a tooth containing a tooth crown includes a step of forming a culture core and a step of forming at least the tooth root in the tooth contained in the culture core; and, if necessary, further includes other steps. In the step of forming at least the tooth root in the tooth contained in the culture core, the culture core is cultured in a medium. In this step, preferably, periodontal tissues (periodontium) are formed in addition to the tooth root.

The above method relates to a method for forming at least a tooth root in a tooth crown-containing tooth derived from mammals such as human and mouse. In particular, this method is useful as a method for forming at least a tooth root in a tooth crown-containing tooth of human.

(Step of Forming Culture Core (Culture Core-forming Step))

The culture core-forming step is a step of forming a culture core containing a tooth and a cell-containing base material, the tooth being wrapped with the cell-containing base material, wherein the cell-containing base material contains at least one kind of cells selected from periodontal ligament-derived cells, bone marrow-derived cells, dental follicle-derived cells, dental pulp-derived cells and dental papilla-derived cells.

<Culture Core>

The culture core contains the tooth crown-containing tooth and the cell-containing base material; and optionally contains, for example, a cell-free porous base material.

—Tooth Containing a Tooth Crown—

The tooth crown-containing tooth is not particularly limited and may be appropriately selected depending on the intended purpose. Examples thereof include a tooth crown itself (i.e., a tooth without tooth roots) and a root-incomplete tooth (i.e., a tooth with tooth roots being formed).

The tooth crown-containing tooth may be, for example, a tooth crown derived from mammals such as human and mouse. In the case of human, for example, there may be used tooth crowns of natural teeth such as third molars (i.e., wisdom teeth) having incomplete tooth roots.

In addition to the natural teeth, the tooth crown-containing tooth may be artificial tooth crowns made of, for example, artificially-produced enamel, dentin and various biological materials.

—Cell-containing Base Material—

The cell-containing base material contains at least one kind of cells selected from periodontal ligament-derived cells, bone marrow-derived cells, dental follicle-derived cells, dental pulp-derived cells and dental papilla-derived cells.

The cell-containing base material is not particularly limited and may be appropriately selected depending on the intended purpose. Examples thereof include a cell sheet and a cell-containing porous base material. One kind of the cell-containing base material may be used, or two or more kinds of the cell-containing base material may be used in combination. In particular, preferably, the tooth crown-containing tooth is wrapped with a cell sheet and further wrapped with a cell-containing porous base material.

The tooth crown-containing tooth is advantageously wrapped with the cell sheet and further wrapped with the cell-containing porous base material, since the tooth root is formed for a short period of time and alveolar bone is formed satisfactorily.

—Periodontal Ligament-derived Cells—

The periodontal ligament-derived cells are not particularly limited and may be appropriately selected depending on the intended purpose. Examples thereof include periodontal ligament fibroblasts, periodontal epithelial cells (epithelial cell rests of Malassez) and periodontal ligament stem cells.

Sources of the periodontal ligament-derived cells are not particularly limited and may be appropriately selected depending on the intended purpose. The periodontal ligament-derived cells may be derived from mammals such as human and mouse. Notably, the periodontal ligament-derived cells and the tooth crown-containing tooth may be derived from the same species or different species.

The method for harvesting the periodontal ligament-derived cells is not particularly limited and may be appropriately selected depending on the intended purpose. For example, the periodontal ligament-derived cells may be harvested from extracted teeth of adult humans or from primary teeth in the mixed dentition period (the period for which primary teeth are replaced with permanent teeth).

—Bone Marrow-derived Cells—

The bone marrow-derived cells are not particularly limited and may be appropriately selected depending on the intended purpose. Examples thereof include bone marrow stromal cells and mesenchymal stem cells.

Sources of the bone marrow-derived cells are not particularly limited and may be appropriately selected depending on the intended purpose. The bone marrow-derived cells may be derived from mammals such as human and mouse. Notably, the bone marrow-derived cells and the tooth crown-containing tooth may be derived from the same species or different species.

The method for harvesting the bone marrow-derived cells is not particularly limited and may be appropriately selected depending on the intended purpose. For example, the bone marrow-derived cells may be harvested through bone-marrow puncture.

—Dental Follicle-derived Cells—

The dental follicle-derived cells are not particularly limited and may be appropriately selected depending on the intended purpose. Examples thereof include dental follicle fibroblasts and dental follicle stem cells.

Sources of the dental follicle-derived cells are not particularly limited and may be appropriately selected depending on the intended purpose. The dental follicle-derived cells may be derived from mammals such as human and mouse. Notably, the dental follicle-derived cells and the tooth crown-containing tooth may be derived from the same species or different species.

The method for harvesting the dental follicle-derived cells is not particularly limited and may be appropriately selected depending on the intended purpose. For example, the dental follicle-derived cells may be harvested from the surrounding tissue of immature teeth of human.

—Dental Pulp-derived Cells—

The dental pulp-derived cells are not particularly limited and may be appropriately selected depending on the intended purpose. Examples thereof include dental pulp fibroblasts and dental pulp stem cells.

Sources of the dental pulp-derived cells are not particularly limited and may be appropriately selected depending on the intended purpose. The dental pulp-derived cells may be derived from mammals such as human and mouse. Notably, the dental pulp-derived cells and the tooth crown-containing tooth may be derived from the same species or different species.

The method for harvesting the dental pulp-derived cells is not particularly limited and may be appropriately selected depending on the intended purpose. For example, the dental pulp-derived cells may be harvested from human extracted teeth or from primary teeth during the mixed dentition.

—Dental Papilla-derived Cells—

The dental papilla-derived cells are not particularly limited and may be appropriately selected depending on the intended purpose. Examples thereof include dental papilla fibroblasts and dental papilla stem cells.

Sources of the dental papilla-derived cells are not particularly limited and may be appropriately selected depending on the intended purpose. The dental papilla-derived cells may be derived from mammals such as human and mouse. Notably, the dental papilla-derived cells and the tooth crown-containing tooth may be derived from the same species or different species.

The method for harvesting the dental papilla-derived cells is not particularly limited and may be appropriately selected depending on the intended purpose. For example, the dental papilla-derived cells may be harvested from root-incomplete (immature) extracted teeth of human.

—Cell Sheet—

The cell sheet is formed as follows. Specifically, at least one kind of cells selected from periodontal ligament-derived cells, bone marrow-derived cells, dental follicle-derived cells, dental pulp-derived cells and dental papilla-derived cells are cultured in a predetermined medium until the cells reach confluency, and then left to stand for at least one week. The thus-treated periodontal ligament-derived cells, bone marrow-derived cells, dental follicle-derived cells, dental pulp-derived cells and dental papilla-derived cells exist as a sheet-like form even after removal from a culture dish. Thus, in the present invention, the cells present in this state are expressed as "cell sheet" for the sake of convenience.

The passage number of the cells used for the cell sheet is not particularly limited, so long as the cells are maintained to be normal karyotyped and diploid cells, and may be appropriately selected depending on the intended purpose. The passage number is preferably up to three, more preferably two. When the passage number is four or more, heteroploid cells (i.e., cells having abnormal chromosomes) may be generated. Whereas when the passage number is two, almost all the cells are normal karyotyped and diploid cells, which is advantageous in terms of safety.

The cell sheet is not particularly limited, so long as it is formed by culturing at least one kind of cells selected from periodontal ligament-derived cells, bone marrow-derived cells, dental follicle-derived cells, dental pulp-derived cells and dental papilla-derived cells in a predetermined medium until the cells reach confluency, followed by being left to stand for one week or longer, and may be appropriately selected depending on the intended purpose. Preferably, the cell sheet is formed by culturing the cells until they reach confluency, followed by being left to stand for one week to four weeks.

The predetermined medium is not particularly limited and may be appropriately selected depending on the intended purpose. For example, DMEM/F12, HAM F12 and α-MEM may be used as the predetermined medium.

The component contained in the medium is not particularly limited and may be appropriately selected depending on the intended purpose. Examples thereof include FBS (fetal bovine serum), non-essential amino acid solution, penicillin, streptomycin and Fungizone.

The culturing method is not particularly limited and may be appropriately selected depending on the intended purpose.

—Cell-containing Porous Base Material—

The cell-containing porous base material contains at least one kind of cells selected from periodontal ligament-derived cells, bone marrow-derived cells, dental follicle-derived cells, dental pulp-derived cells and dental papilla-derived cells.

The porous base material used for the cell-containing porous base material is not particularly limited and may be appropriately selected depending on the intended purpose. Examples thereof include TERDERMIS and TERUPLUG (registered trademarks, these products are of Olympus Terumo Biomaterials Corp.), collagen sponge (product of KOKEN CO., LTD.), collagen sponge (product of Nitta Gelatin Inc.), CELL MATRIX (registered trademark, collagen gel for tissue culture, product of Nitta Gelatin Inc.), BD MATRIGEL (registered trademark, product of Becton Dickinson), polyglycolic acid (PGA) sheet (product of Albany international research Co.) and poly DL-lactide-co-glycoside (PLGA, product of Sigma Co.).

The above porous base materials are preferably used for the following reasons. Specifically, numerous cells can be three-dimensionally arranged in local places thereon, to thereby effectively obtain the functions of each cell and the interactions between the cells. Thus, the porous base materials can provide a place where a tooth root and periodontal tissue made of various tissues (e.g., cementum, periodontal ligament, alveolar bone and gingiva) can be three-dimensionally formed.

The method for incorporating into the porous base material at least one kind of cells selected from periodontal ligament-derived cells, bone marrow-derived cells, dental follicle-derived cells, dental pulp-derived cells and dental papilla-derived cells is not particularly limited and may be appropriately selected depending on the intended purpose. Examples thereof include a method in which a cell suspension is applied to the porous base material, followed by culturing; and a method in which the porous base material is placed on the cultured cells, so that the cells are transferred into the porous base material.

The cell concentration of the suspension liquid in the above method, in which the suspension liquid of the cells is applied to the porous base material, is not particularly limited and may be appropriately selected depending on the intended purpose. The cell concentration may be, for example, $1 \times 10^6$ cells/mL or $2 \times 10^7$ cells/mL.

Also, the culturing period in the above method, in which the suspension liquid of the cells is applied to the porous base material, is not particularly limited and may be appropriately selected depending on the intended purpose. The culturing period is preferably 72 hours or longer, more preferably about 72 hours to about one week.

—Cell-free Porous Base Material—

A porous base material used for the cell-free porous base material is not particularly limited and may be appropriately selected depending on the intended purpose. The porous base material may be the same as those described in the cell-containing porous base material.

—Wrapping Method—

The method for wrapping the tooth crown-containing tooth with the cell-containing base material is not particularly limited and may be appropriately selected depending on the intended purpose. When the cell sheet is used as the cell-containing base material, for example, the cell sheet is divided with a sterile knife, and the tooth crown-containing tooth is wrapped with the appropriate sized cell sheet.

The method for further wrapping the tooth, which has been wrapped with the cell sheet, with the cell-containing porous base material or the cell-free porous base material is not particularly limited and may be appropriately selected depending on the intended purpose.

<Pre-culturing Step>

The culture core-forming step may include a pre-culturing step.

The pre-culturing step is a step of culturing the tooth crown-containing tooth on the cell sheet.

The pre-culturing period is not particularly limited and may be appropriately selected depending on the intended purpose. The pre-culturing period is preferably 0.5 days to 7 days, more preferably 1 day to 2 days.

The pre-culturing allows the tooth crown-containing tooth to be fixed and immobilized on the cell sheet, which facilitates wrapping of the tooth crown-containing tooth with the cell sheet. The pre-culturing has another advantage that soluble factors produced by the cell sheet can induce various cells (e.g., dental papilla cells (dental pulp cells), enamel epithelial cells, Hertwig's epithelial sheath cells and dental follicle cells) present on the tooth crown-containing tooth into tooth roots and periodontal tissue-forming cells.

Notably, instead of the pre-culturing step, the tooth crown-containing tooth may be immersed for several hours in a conditioned medium of at least one kind of cells selected from periodontal ligament-derived cells, bone marrow-derived cells, dental follicle-derived cells, dental pulp-derived cells and dental papilla-derived cells.

(Step of Forming at Least a Tooth Root of the Tooth Contained in the Culture Core)

The step of forming at least a tooth root in the tooth contained in the culture core is a step of culturing the culture core in a medium so as to form at least the tooth root in the tooth contained in the culture core. In this step, preferably, periodontal tissues (periodontium) are formed in addition to the tooth root.

<Medium>

The medium for the culture core contains a component contained in a conditioned medium of a serum-free-cultured cell line of a human uterocervical squamous carcinoma cell line (hereinafter may be referred to as "natural ETFs" (embryotrophic factors)), an additive containing at least one selected from IL-1β, IL-6, IL-8, IL-9, EGF, IGF-I, GH, PDGF-AB, VEGF, LIF, HGF, FGF-2, FGF-1, BMP-2, BMP-4, M-CSF, dexamethasone, insulin, thyroxine, thyrocalcitonin, ascorbic acid and β-glycerophosphate(corresponding to "synthetic ETFs", hereinafter may be referred to as "recombinant human Organ Engineering Factors: rhOEFs"), or both of the component and the additive; and, if necessary, further contains other components.

The medium for the culture core is not particularly limited and may be appropriately selected depending on the intended purpose. Examples thereof include DMEM/F12, Ham F12 and α-MEM.

The medium may contain the above natural ETFs, the above rhOEFs, or both of them. Preferably, the rhOEFs are used alone since they do not contain unknown infective materials.

—Natural ETFs—

The natural ETFs are components contained in the conditioned medium of the serum-free-cultured cell line (SKG-II-SF) of a human uterocervical squamous carcinoma cell line (SKG-II).

The method for preparing the natural ETFs is not particularly limited and may be appropriately selected depending on the intended purpose. In one exemplary method, the SKG-II-SF cells are cultured, and the culture medium is collected, desalted and then freeze-dried.

The culturing period for the SKG-II-SF cells is not particularly limited and may be appropriately selected depending on the intended purpose. For example, the SKG-II-SF cells are cultured at the state of confluency for 4 days.

The natural ETFs contains at least IL-1α, IL-1β, IL-2, IL-3, IL-4, IL-5, IL-6, IL-9, IL-10, IL-12, EGF, TNF-α, TGF-α, IGF-I, GH, PDGF-AB, IGF-BP-3, FGF-2, VEGF, LIF and HGF; and further contains other components (derived from the conditioned medium).

The amounts of the components generally contained in the natural ETFs are as follows, for example.

IL-1α (Interleukin-1α): ≤3.0 pg/mL
IL-1β (Interleukin-1β): 100 pg/mL to 200 pg/mL
IL-2 (Interleukin-2): ≤5.0 pg/mL
IL-3 (Interleukin-3): ≤31 pg/mL
IL-4 (Interleukin-4): ≤2.0 pg/mL
IL-5 (Interleukin-5): ≤5.0 pg/mL
IL-6 (Interleukin-6): 50 pg/mL to 150 pg/mL
IL-9 (Interleukin-9): 400 pg/mL to 500 pg/mL
IL-10 (Interleukin-10): ≤5.0 pg/mL
IL-12 (Interleukin-12): ≤7.8 pg/mL
EGF (Epidermal growth factor): 0.5 ng/mL to 2.0 ng/mL
TNF-α (Tumor necrosis factor-α): ≤5.0 pg/mL
TGF-α (Transforming growth factor-α): ≤5.0 pg/mL
IGF-I (Insulin-like growth factor-I): ≤6.3 ng/mL GH (Growth Hormone): 0.1 ng/mL to 0.5 ng/mL
PDGF-AB (Platelet-derived growth factor-AB): 450 pg/mL to 550 pg/mL
IGF-BP-3 (Insulin-like growth factor-binding protein-3): ≤0.2 μg/mL
FGF-2 (Fibroblast growth factor): 35 pg/mL to 45 pg/mL
VEGF (Vascular endothelial growth factor): 1 ng/mL to 10 ng/mL
LIF (Leukemia inhibitory factor): 25 pg/mL to 35 pg/mL
HGF (Hepatocyte growth factor): 0.5 ng/mL to 1.5 ng/mL The amount of the natural ETFs contained in the medium for the culture core is not particularly limited and may be appropriately selected depending on the intended purpose. The amount thereof is preferably 1% by volume to 12% by volume, more preferably 5% by volume to 10% by volume. When the amount of the natural ETFs contained in the medium is less than 1% by volume or more than 12% by volume, it may be difficult to form a tooth root, periodontal tissue or a complex structure thereof. When the amount of the natural ETFs falls within the above preferred range, it is advantageous in that a tooth root, periodontal tissue or a complex structure thereof is efficiently formed.

—rhOEFs—

The rhOEFs contain at least one selected from IL-1β, IL-6, IL-8, IL-9, EGF, IGF-I, GH, PDGF-AB, VEGF, LIF, HGF, FGF-2, FGF-1, BMP-2, BMP-4, M-CSF, dexamethasone, insulin, thyroxine, thyrocalcitonin, ascorbic acid and β-glycerophosphate; and, if necessary, further contains other components.

The component of the above rhOEFs is not particularly limited and may be appropriately selected depending on the intended purpose. Preferably, commercially available products thereof are used since they do not contain unknown infective materials.

In the medium for the culture core, the amounts of the components of the rhOEFs are not particularly limited and may be appropriately selected depending on the intended purpose. The amounts thereof are preferably equal to or more than those given below.

IL-1β (Interleukin-1β): 150 pg/mL
IL-6 (Interleukin-6): 100 pg/mL
IL-8 (Interleukin-8): 1.0 ng/mL
IL-9 (Interleukin-9) 450 pg/mL
EGF (Epidermal growth factor): 1.5 ng/mL
IGF-I (Insulin-like growth factor-I): 20 ng/mL
GH (Growth Hormone): 2.5 ng/mL
PDGF-AB (Platelet-derived growth factor-AB): 0.6 ng/mL
VEGF (Vascular endothelial growth factor): 3.2 ng/mL
LIF (Leukemia inhibitory factor): 35 pg/mL
HGF (Hepatocyte growth factor): 1.0 ng/mL
FGF-2 (Fibroblast growth factor-2): 20 ng/mL
FGF-1 (Fibroblast growth factor-1): 5.0 ng/mL
BMP-2 (Bone morphogenetic protein-2): 10 ng/mL
BMP-4 (Bone morphogenetic protein-4): 15 ng/mL
M-CSF (Macrophage-colony stimulating factor): 10 μg/mL
Dexamethasone: 5 μM
Insulin: 7.5 ng/mL
Thyroxine: 5.5 ng/mL
Thyrocalcitonin: 10 ng/mL
Ascorbic acid: 50 μg/mL
β-Glycerophosphate: 10 mM When the amounts of the components of the rhOEFs contained in the medium are less than the above-given amounts, it may be difficult to form a tooth root, periodontal tissue or a complex structure thereof.

The method for adding the rhOEFs to the medium is not particularly limited and may be appropriately selected depending on the intended purpose. Examples thereof include a method in which all of the above components are added to the medium and a method in which some of the above components are added to the medium in various combinations.

—Other Component—

The other components contained in the medium for the culture core are not particularly limited and may be appropriately selected depending on the intended purpose. Examples thereof include FBS.

—Concentration of β-glycerophosphate—

The amount of β-glycerophosphate added to the medium for the culture core is not particularly limited and may be appropriately selected depending on the intended purpose. The amount thereof is particularly preferably 10 mM.

When the concentration of β-glycerophosphate in the medium is less than 10 mM, a tooth root, periodontal tissue or a complex structure thereof may be insufficiently formed. When the concentration of β-glycerophosphate in the medium is more than three times of that concentration, a tooth root, periodontal tissue or a complex structure thereof may not be formed. When the concentration is the particularly preferred value, hard tissues (dentin, cementum and alveolar bone) can be efficiently formed, which is preferred.

<Culturing>

The method for culturing the culture core is not particularly limited and may be appropriately selected depending on the intended purpose. Preferred examples thereof include a static culture method and a circumfusion culture method.

The culturing period for the culture core may be appropriately determined depending on the formation of a tooth root, periodontal tissue or a complex structure thereof.

For example, when the static culture method is used, preferably, the culturing period is 3 weeks to 4 weeks in the case of mouse and is 24 weeks in the case of human. When the circumfusion culture method is used, the culturing period can be further shortened.

The interval at which the medium is changed in the culturing (static culture method) is not particularly limited and may be appropriately selected depending on the intended purpose. The medium is preferably changed every 4 days or 5 days, more preferably every 3 days or 4 days, particularly preferably every 2 days or 3 days.

[Regenerated Tooth]

A regenerated tooth of the present invention can be obtained by the above-described method of the present invention. In a first embodiment, the regenerated tooth of the present invention contains at least a tooth crown and a tooth root. In a second embodiment, the regenerated tooth of the present invention contains at least a tooth crown, a tooth root and periodontal tissues (periodontium).

The periodontal tissues contain periodontal ligament, alveolar bone, cementum and gingiva.

The regenerated tooth of the present invention may be directly used for transplantation or may be transplanted after processing such as shaping. Alternatively, after the periodontal tissue has been removed, the remaining tooth may be used for transplantation into tooth loss region.

EXAMPLES

The present invention will next be described by way of Examples, which should not be construed as limiting the present invention thereto.

Example 1

(Formation of Tooth Root and Periodontal Tissues Using Mouse Tooth Crown and Periodontal Ligament-derived Cell Sheet)

<Formation of Culture Core>

—Preparation of Tooth Crown—

The mandibular first molars were extracted from 6-day-old neonatal mice. As shown in FIG. 1, in each molar (hereinafter may be referred to as "mouse tooth crown"), the tooth crown was formed completely but the tooth root was not formed yet.

—Preparation of Periodontal Ligament-derived Cell Sheet—

Figure 2:
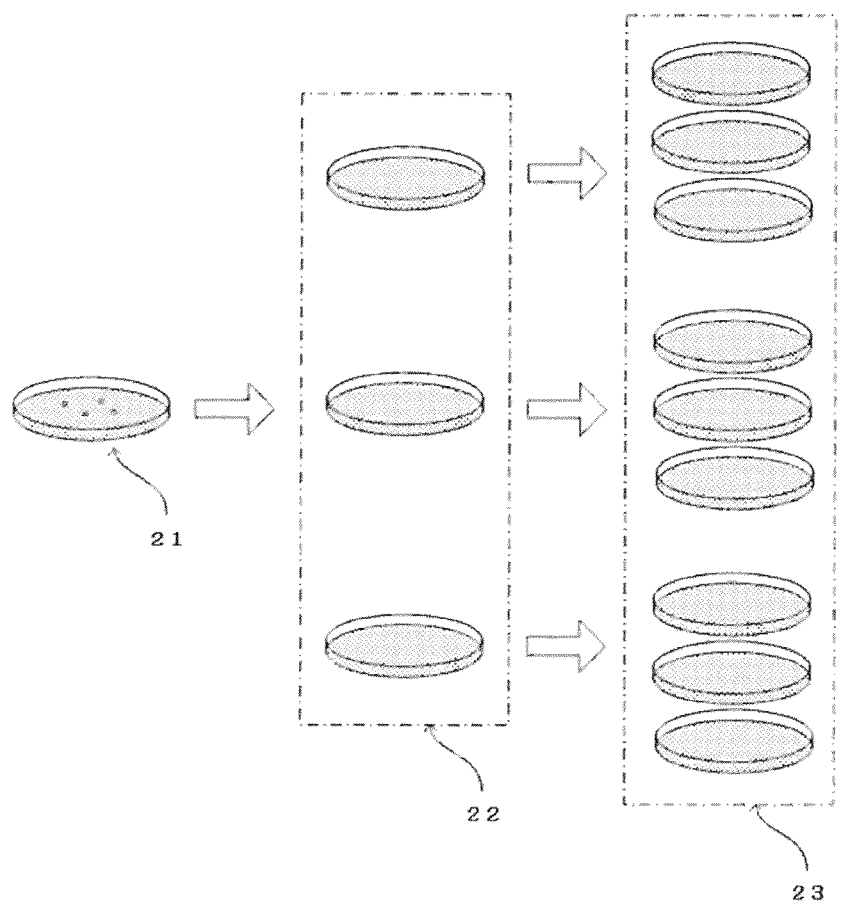
FIG. 2 illustrates subculture protocol of periodontal ligament-derived cells in Example 1.

The periodontal ligament tissue was separated from the surface of the tooth root of an extracted tooth of adult human with a single-edged razor blade, to thereby obtain fragments of the tissue. The thus-obtained periodontal ligament tissue was further cut with a double-edged razor blade and were added to 0.1% trypsin-0.02% EDTA/PBS (−). The resultant mixture was heated at 37° C. for 30 min, and then strongly pipetted to isolate periodontal ligament-derived cells. Subsequently, a liquid containing the periodontal ligament-derived cells was centrifugated at 300×g for 5 min. After removal of the supernatant through aspiration, a basal medium (DMEM/F12 (product of Invitrogen Co.)+15% FBS (product of Moregate BioTech Co., Lot No. 24300113)+1% non-essential amino acid liquid (product of Invitrogen Co.)+50 U/mL Penicillin (product of Invitrogen Co.)+50 µg/mL Streptomycin (product of Invitrogen Co.)+0.25 µg Fungizone (product of Invitrogen Co.)) was added to the precipitate, followed by primarily culturing in a culture dish (indicated by reference numeral 21 in FIG. 2). The primary cultures, after reached confluency, were divided into three dishes, where the periodontal ligament-derived cells were subcultured (passage 1, indicated by reference numeral 22 in FIG. 2). After reached confluency, the subcultured cells (passage 1) in each culture dish were further divided into three culture dishes, where the periodontal ligament-derived cells were subcultured (passage 2, indicated by reference numeral 23 in FIG. 2.). After the periodontal ligament-derived cells (passage 2) had reached confluency, sheets formed of the periodontal ligament-derived cells were used as periodontal ligament-derived cell sheets. FIG. 2 illustrates subculturing protocol of periodontal ligament-derived cells.

—Pre-culturing—

Figure 3:
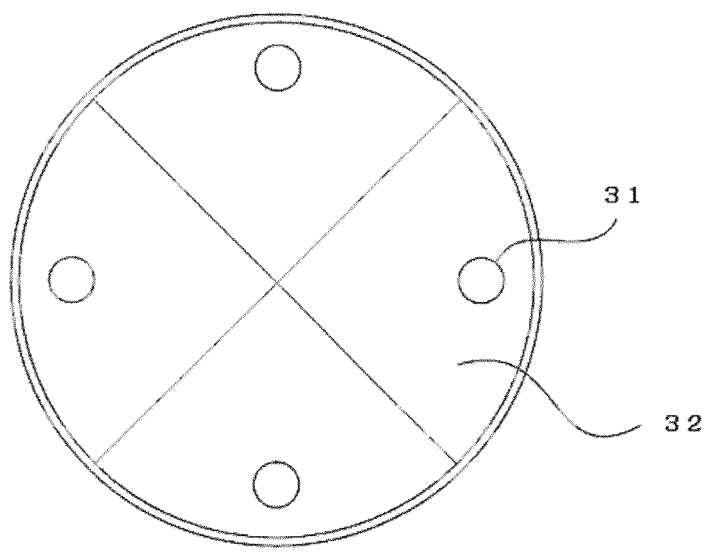
FIG. 3 illustrates pre-culture in Example 1.

The above mouse tooth crowns (indicated by reference numeral 31 in FIG. 3) were placed on the cell sheet (indicated by reference numeral 32 in FIG. 3) of the human periodontal ligament-derived cells cultured as described above (4 tooth crowns per culture dish), followed by culturing (pre-culturing) for 2 days. FIG. 3 is an explanatory view of pre-culturing.

Through this pre-culturing, the mouse tooth crowns were fixed on the human periodontal ligament-derived cell sheet.

—Culture Core—

Figure 4:
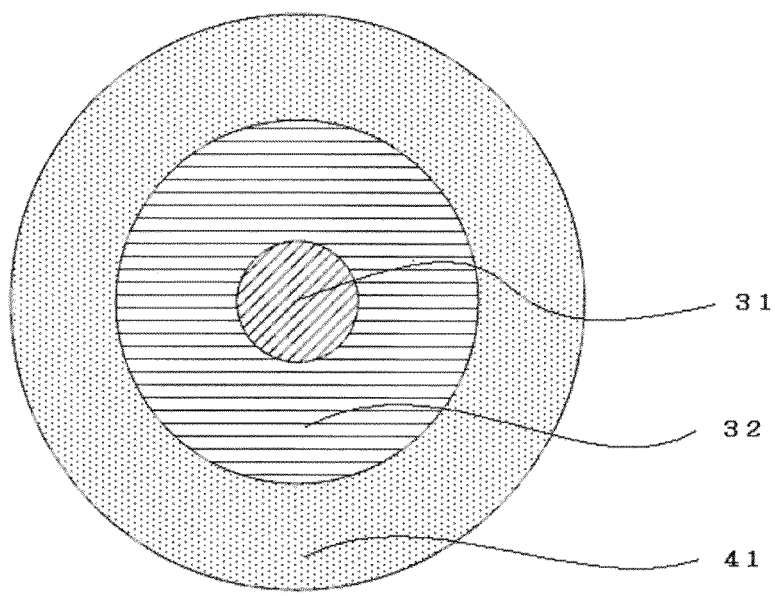
FIG. 4 illustrates the cross-section of the culture core in Example 1.

After pre-culturing, the human periodontal ligament-derived cell sheet having the mouse tooth crowns thereon was cut with a sterile razor blade so as to have a predetermined size. The thus-cut sheets were separated from the culture dish with a rubber policeman (product of TPP Co.), so that the mouse tooth crowns were wrapped with human periodontal ligament-derived cell sheets. Thereafter, the mouse tooth crowns, which had been wrapped with the human periodontal ligament-derived cell sheets, were further wrapped with TERDERMIS (registered trademark) (product of Olympus Terumo Biomaterials Corp.). In this manner, a culture core illustrated in FIG. 4 was obtained, which had the tooth crown (indicated by reference numeral 31 in FIG. 4) embedded in the human periodontal ligament-derived cell sheet (indicated by reference numeral 32 in FIG. 4) and TERDERMIS (indicated by reference numeral 41 in FIG. 4). FIG. 4 is an explanatory view of the cross-section of the culture core.

<Formation of Tooth Root and Periodontal Tissue>

The culture core was cultured in a medium prepared by adding natural ETFs (0.1 mL/mL) to a 15% FBS-containing DMEM/F12 medium. The medium was changed every several days. Notably, the above natural ETFs were prepared as follows.

—Preparation of Natural ETFs—

Cells of a serum-free-cultured cell line (SKG-II-SF, obtained from RIKEN BIORESOURCE CENTER CELL BANK, registration number: RCB0685) of human uterocervical squamous carcinoma cell line (SKG-II) were cultured for 4 days using DMEM/F12 or Ham F12 as a medium. Then, the conditioned medium was recovered, desalted and freeze-dried to thereby prepare natural ETFs.

After immunological analysis through ELISA (enzyme-linked immunosorbent assay) and radioimmunoassay, the above natural ETFs were found to contain the following components.

IL-1α: ≤3.0 pg/mL
IL-1β: 163 pg/mL
IL-2: ≤5.0 pg/mL
IL-3: ≤31 pg/mL
IL-4: ≤2.0 pg/mL
IL-5: ≤5.0 pg/mL
IL-6: 104 pg/mL
IL-9: 453 pg/mL
IL-10: ≤5.0 pg/mL
IL-12: ≤7.8 pg/mL
EGF: 1.3 ng/mL
TNF-α: ≤5.0 pg/mL
TGF-α: ≤5.0 pg/mL
IGF-I: ≤6.3 ng/mL
GH: 0.17 ng/mL
PDGF-AB: 510 pg/mL
IGF-BP-3: ≤0.2 µg/mL
FGF-2: 37 pg/mL
VEGF: ≤1,000 pg/mL
LIF: 31 pg/mL
HGF: 1.1 ng/mL

—One Week After Culturing—

Figure 5:
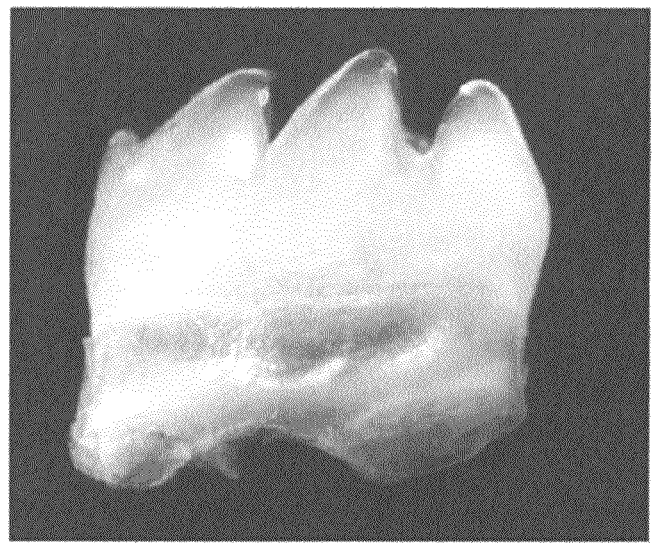
FIG. 5 is an explanatory view (stereomicroscope image) of the mouse tooth crown cultured for one week in Example 1.

One week after the initiation of culturing, the tooth was taken out and examined for the formation of tooth roots. FIG. 5 is an explanatory view (stereomicroscope image) of the mouse tooth crown cultured for one week. As shown in FIG. 5, it was confirmed that the furcation area was fused and two tooth roots were formed.

—Two Weeks After Culturing—

Figure 6:
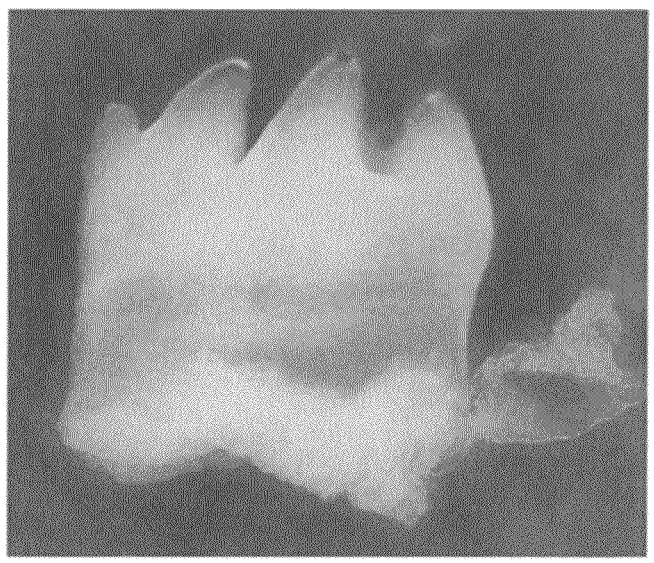
FIG. 6 is an explanatory view (stereomicroscope image) of the mouse tooth crown cultured for two weeks in Example 1.

Two weeks after the initiation of culturing, the tooth was taken out and examined for the formation of tooth roots. FIG. 6 is an explanatory view (stereomicroscope image) of the mouse tooth crown cultured for two weeks.

As shown in FIG. 6, it was confirmed that the two tooth roots were further elongated.

—Four Weeks After Culturing—

Figure 7:
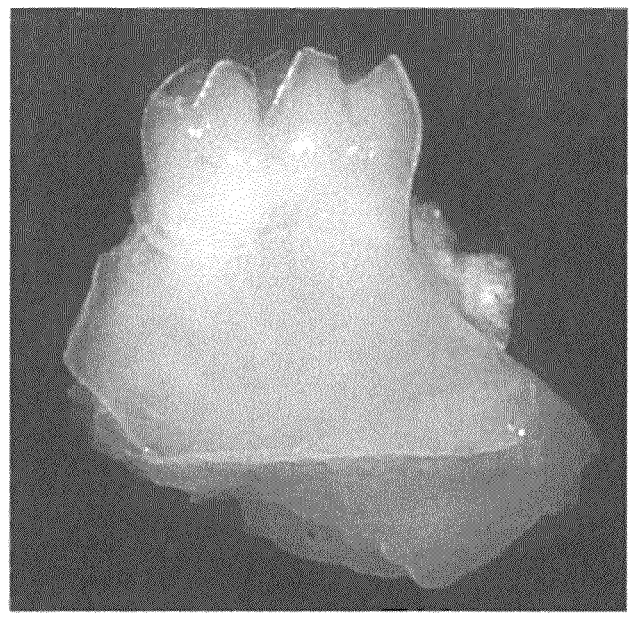
FIG. 7 is an explanatory view (stereomicroscope image) of the mouse tooth crown cultured for four weeks in Example 1.

Four weeks after the initiation of culturing, the tooth was taken out and examined for the formation of tooth roots. FIG. 7 is an explanatory view (stereomicroscope image) of the mouse tooth crown cultured for four weeks.

As shown in FIG. 7, it was confirmed that alveolar bone was formed in part corresponding to the tooth roots.

—Soft X-ray Image—

Figure 8:
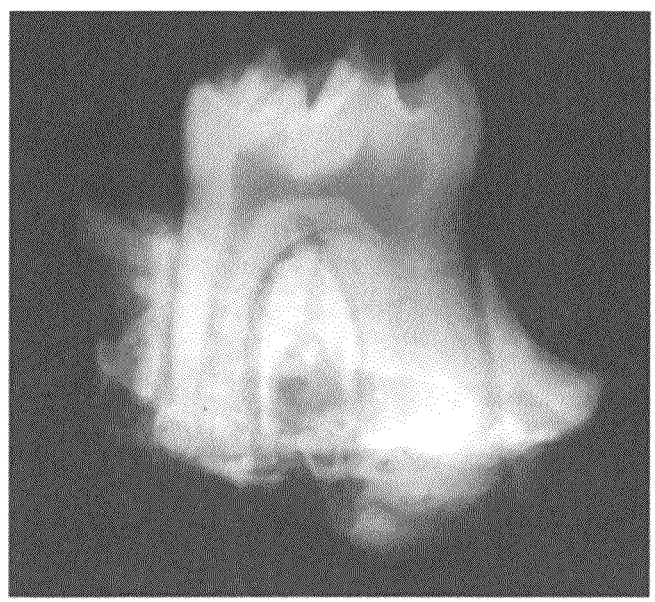
FIG. 8 is a soft X-ray image of the tooth cultured for four weeks in Example 1.

FIG. 8 is a soft X-ray image of the tooth cultured for four weeks. As shown in FIG. 8, alveolar bone was formed in addition to the tooth roots. And, it was confirmed that a periodontal ligament space (which is indicative of formation of periodontal ligament (soft tissue)) was formed between the tooth roots and the alveolar bone.

—HE (Hematoxylin-eosin) Staining—

Figure 9:
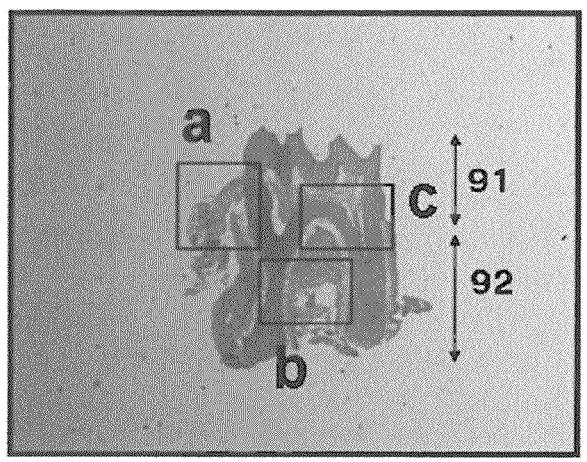
FIG. 9 is an explanatory view of a thin section of the four-week-cultured tooth having undergone HE staining in Example 1.

FIG. 9 is an explanatory view of a thin section of the four-week-cultured tooth having undergone HE staining. In FIG. 9, reference numeral "91" denotes a tooth crown and reference numeral "92" denotes a "tooth root."

Figure 10:
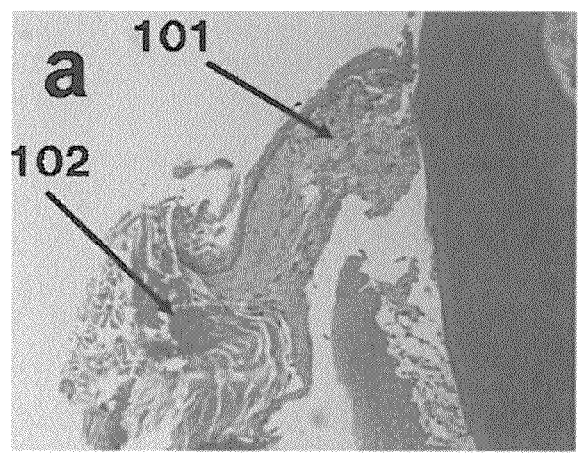
FIG. 10 is an enlarged image of the boxed region denoted by "a" in FIG. 9.

FIG. 10 is an enlarged image of the boxed region denoted by "a" in FIG. 9. The boxed region "a" is part of the tissue surrounding the tooth crown. As shown in FIG. 10, it was confirmed that gingiva 101 and muscle tissue 102 were formed around the tooth crown.

Figure 11:
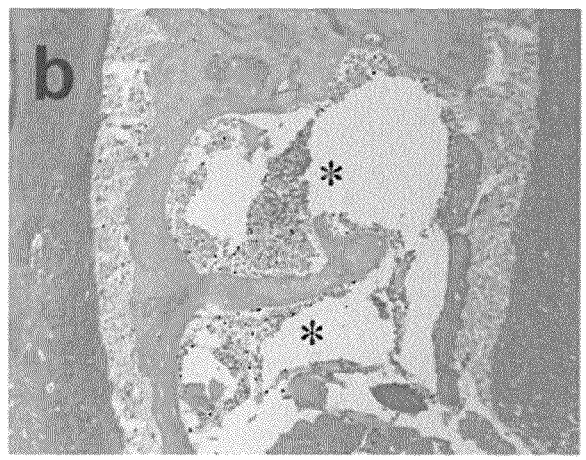
FIG. 11 is an enlarged image of the boxed region denoted by "b" in FIG. 9.

FIG. 11 is an enlarged image of the boxed region denoted by "b" in FIG. 9. The boxed region "b" is part of bone tissue between the two tooth roots. As shown in FIG. 11, numerous erythroblasts were observed in bone marrow of the newly formed alveolar bone, indicating hematopoiesis. In FIG. 11, the regions indicated by symbol "*" are medullary cavities.

Figure 12:
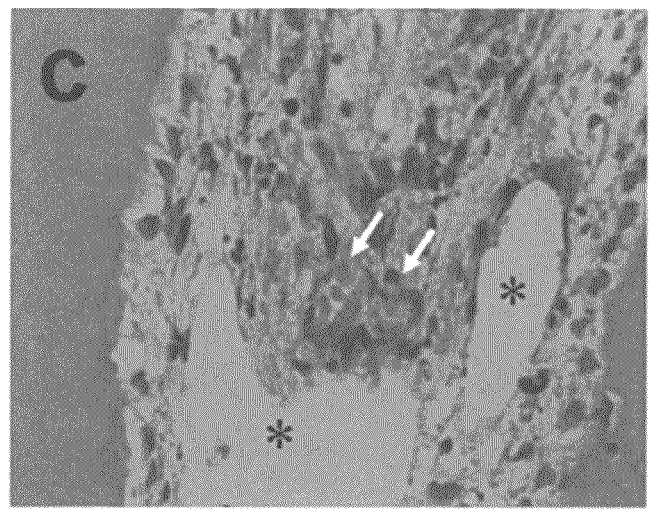
FIG. 12 is an enlarged image of the boxed region denoted by "c" in FIG. 9.

FIG. 12 is an enlarged image of the boxed region denoted by "c" in FIG. 9. The boxed region "c" is part of radicular pulp. As shown in FIG. 12, it was confirmed that angiogenesis involving generation of erythrocytes was observed in radicular pulp (indicated by the arrows). In FIG. 12, the regions indicated by symbol "*" are vascular lumens.

Figure 13:
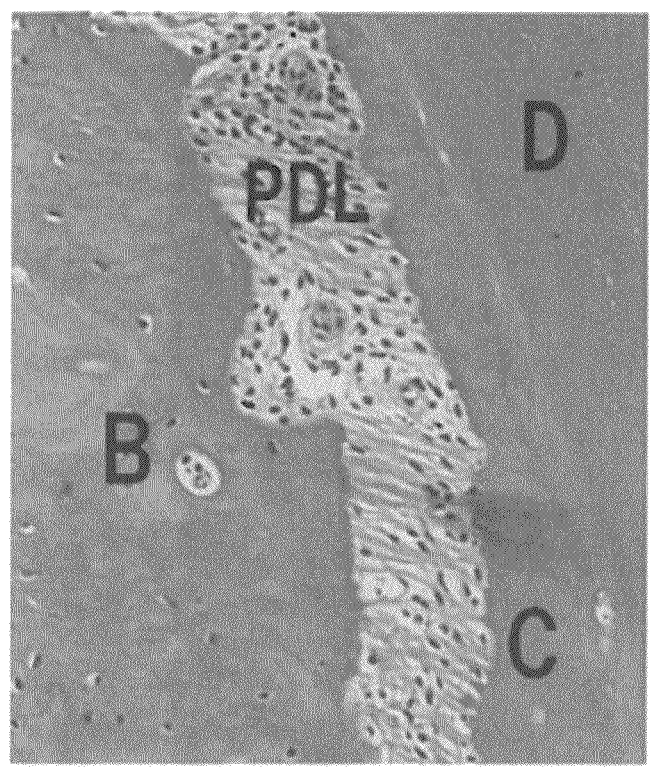
FIG. 13 is an enlarged image (HE-stained image) of the periodontal tissues cultured for four weeks in Example 1.

FIG. 13 is an enlarged image of the periodontal tissues of the tooth cultured for four weeks (HE-stained image). As shown in FIG. 13, it was confirmed that periodontal ligament (PDL; corresponding to the periodontal ligament space in the soft X-ray image of FIG. 8) was formed between alveolar bone (B) and the region of cementum (C) and dentin (D).

—In Situ Hybridization—

Through in situ hybridization, the regenerated tissue was examined in terms of gene expression. Periostin was used as a marker of periodontal ligament, and bone sialoprotein (BSP) was used as a marker of bone and cementum.

Figure 14:
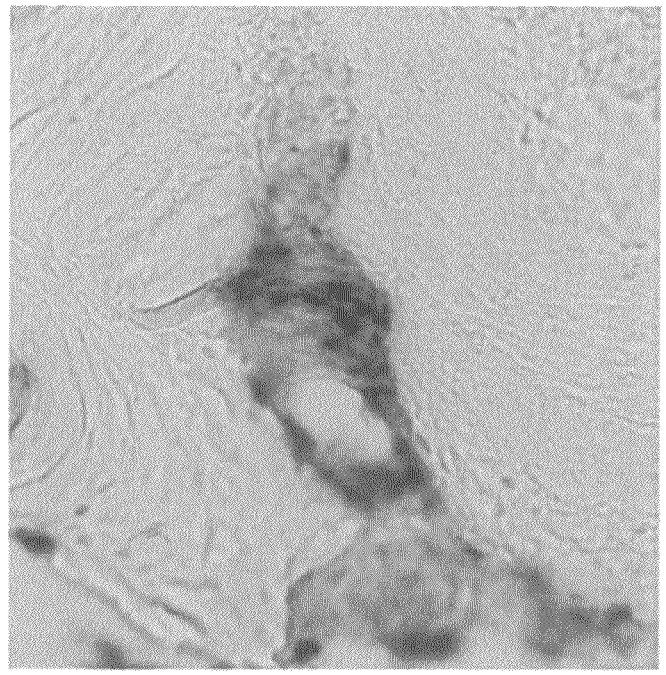
FIG. 14 is a photograph showing the results of the in situ hybridization for periostin in Example 1.
Figure 15:
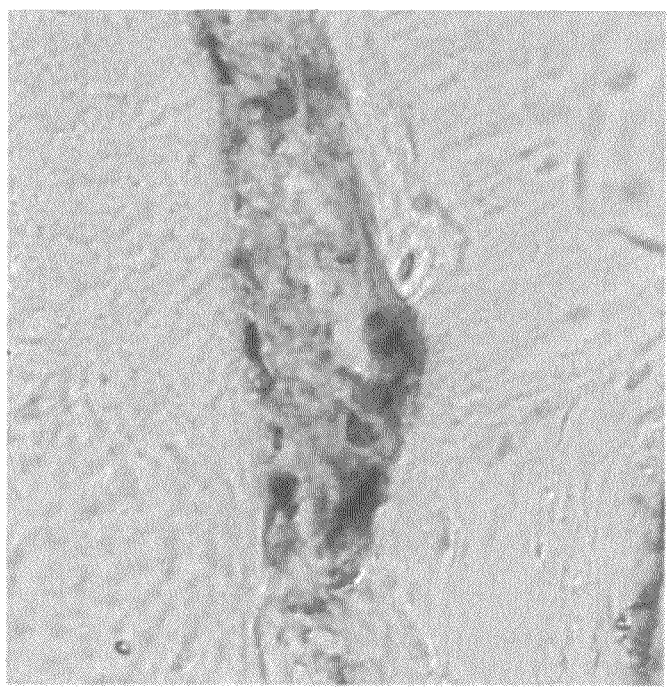
FIG. 15 is a photograph showing the results of the in situ hybridization for bone sialoprotein (BSP) in Example 1.

FIG. 14 is a photograph showing the results of the in situ hybridization for periostin. FIG. 15 is a photograph showing the results of the in situ hybridization for BSP. As shown in FIGS. 14 and 15, the fact that the regenerated tissue had been periodontal tissue (periodontium) was confirmed on the gene expression level using these markers specific to periodontal ligament, bone and cementum. This also indicates that periodontal tissue was formed around the tooth root elongated after culturing.

<Transplant Test 1>

—Test for Whether Tooth is Engrafted—

The four-week-cultured tooth was transplanted in the cavity formed after the incisor had been extracted from the upper jaw of mouse.

Figure 16:
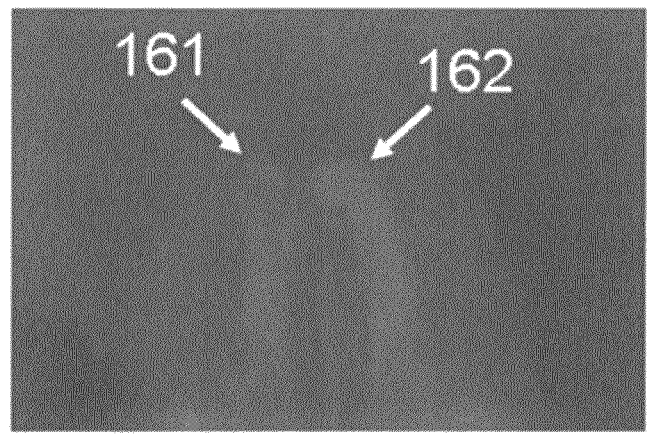
FIG. 16 is a dental X-ray image of the tooth transplanted for four weeks in Example 1.
Figure 17:
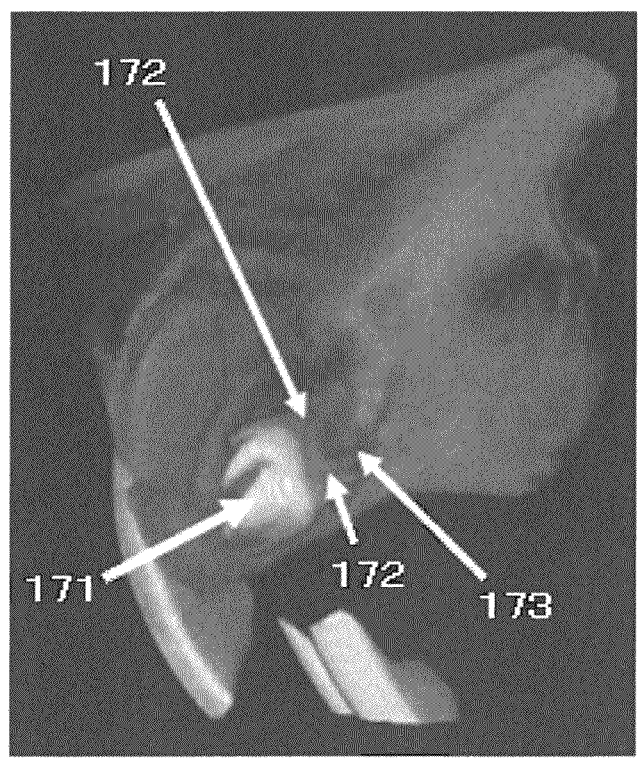
FIG. 17 is a micro-CT image of the tooth transplanted for four weeks in Example 1.

Four weeks after transplantation, the maxillary incisor region was photographed to obtain a dental X-ray image and a micro-CT image. FIG. 16 is a dental X-ray image of the tooth transplanted for four weeks. FIG. 17 is a micro-CT image of the tooth transplanted for four weeks. In FIG. 16, reference numeral 161 denotes the transplanted tooth and reference numeral 162 denotes the normal incisor (residing on the opposite side). In the transplanted tooth of FIG. 17, reference numeral 171 denotes a tooth crown, reference numeral 172 denotes tooth roots (2 roots) and reference numeral 173 denotes a periodontal ligament space.

As shown in FIGS. 16 and 17, it was confirmed that the transplanted tooth was maintained in jawbone and engrafted.

<Transplant Test 2>

—Confirmation of Vascular Invasion—

The tooth cultured for 10 weeks was transplanted in cranial bone of mouse. Nine weeks after transplantation, fluorescently-labeled liquid gelatin was perfused from the heart of the mouse and tissue sections were obtained. Thereafter, the presence or absence of blood vessels in the transplanted tooth was confirmed under a confocal laser microscope.

Figure 18A:
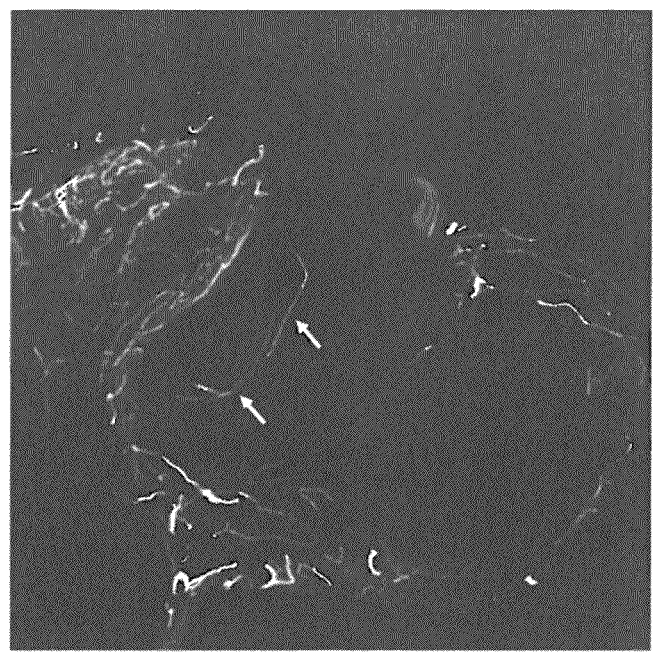
FIG. 18A is a fluorescent image of the tooth transplanted in mouse cranial bone in Example 1.
Figure 18B:
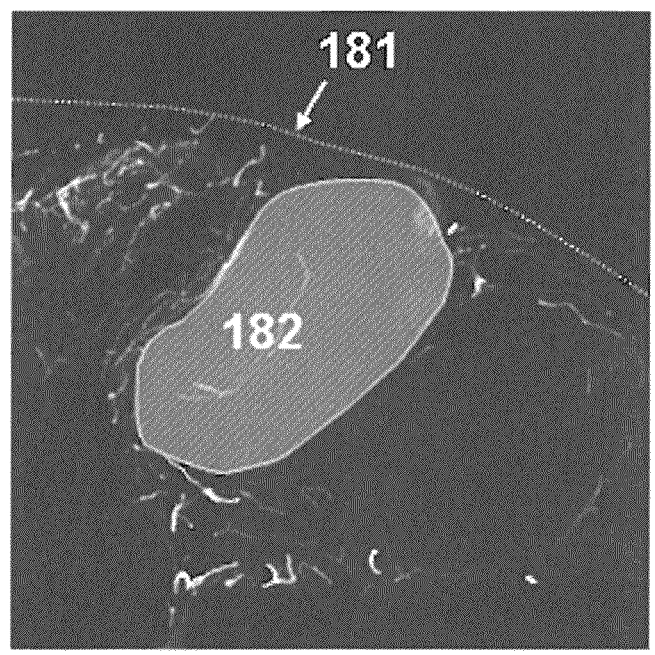
FIG. 18B is a fluorescent image of the tooth transplanted in mouse cranial bone in Example 1.

FIGS. 18A and 18B are fluorescent images of the transplanted tooth in the mouse cranial bone. In FIG. 18B, reference numeral 181 denotes a cranial bone wall and reference numeral 182 denotes the transplanted tooth.

As shown in FIGS. 18A and 18B, it was confirmed that host-derived capillary vessels invaded into the dental pulp of the transplanted tooth (indicated by the arrows in FIG. 18A) and that the transplanted tooth was engrafted.

Example 2

(Formation of Tooth Root and Periodontal Tissue Using Human Tooth Crown and Periodontal Ligament-Derived Cell Sheet)

<Formation of Culture Core>

—Preparation of Tooth Crown—

Figure 19:
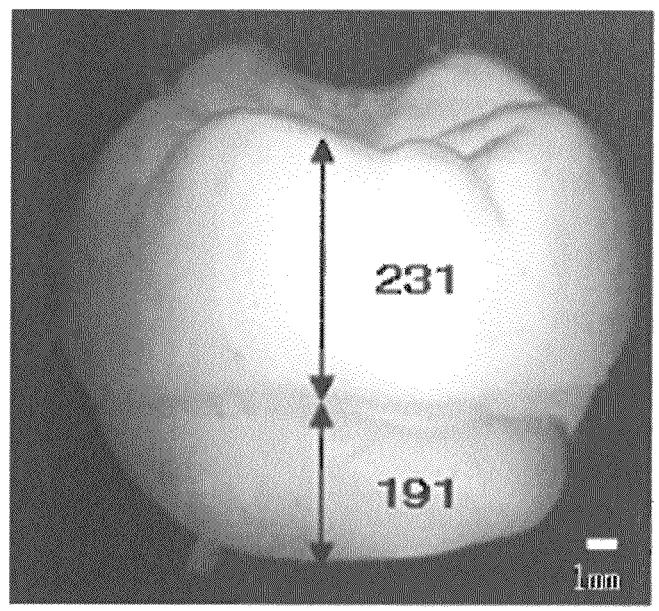
FIG. 19 is an explanatory view (stereomicroscope image) of the human tooth crown used in Example 2.

The human tooth crown used was an extracted third molar (i.e., a wisdom tooth) without tooth root (no tooth root), which had been taken from a 13-year-old female patient. FIG. 19 is an explanatory view (stereomicroscope image) of the human tooth crown. In FIG. 19, reference numeral 231 denotes the tooth crown and reference numeral 191 denotes a dental papilla. As shown in FIG. 19, the tooth crown was completed while tooth roots were not formed.

—Preparation of Periodontal Ligament-derived Cell Sheet—

A periodontal ligament-derived cell sheet was prepared in the same manner as in Example 1.

—Pre-culturing—

Figure 20:
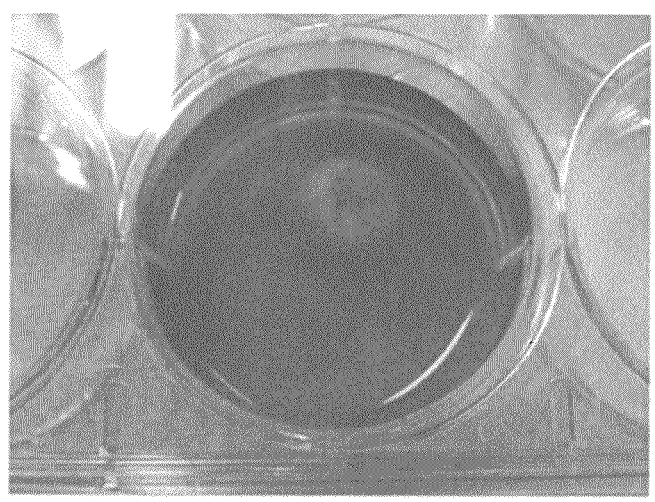
FIG. 20 is an explanatory view (stereomicroscope image) of pre-culture in Example 2.

The human tooth crown was placed on the periodontal ligament-derived cell sheet, followed by culturing (pre-culturing) for 2 days in this state. FIG. 20 is an explanatory view (stereomicroscope image) of pre-culturing.

—Wrapping—

In the same manner as in Example 1, the pre-cultured human tooth crown was wrapped with the human periodontal ligament-derived cell sheet and TERDERMIS (registered trademark), to thereby obtain a culture core.

<Formation of Tooth Root and Periodontal Tissue>

Figure 21:
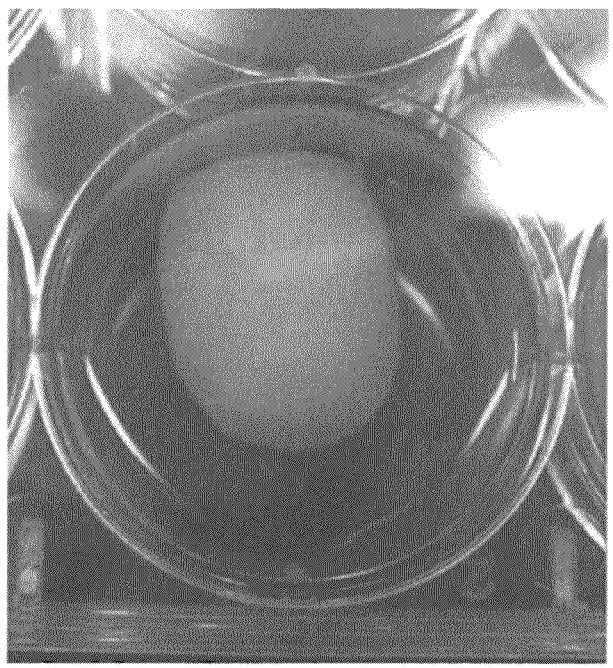
FIG. 21 is an explanatory view (stereomicroscope image) of the culture core in Example 2.

The thus-obtained culture core was cultured in the following medium: 15% FBS-containing DMEM/F12 medium containing natural ETFs at 0.1 mL/mL. The medium was changed every a few days. FIG. 21 is an explanatory view (stereomicroscope image) of the culture core. Notably, the natural ETFs were prepared in the same manner as in Example 1.

—Twenty-four Weeks After Culturing—

Figure 22:
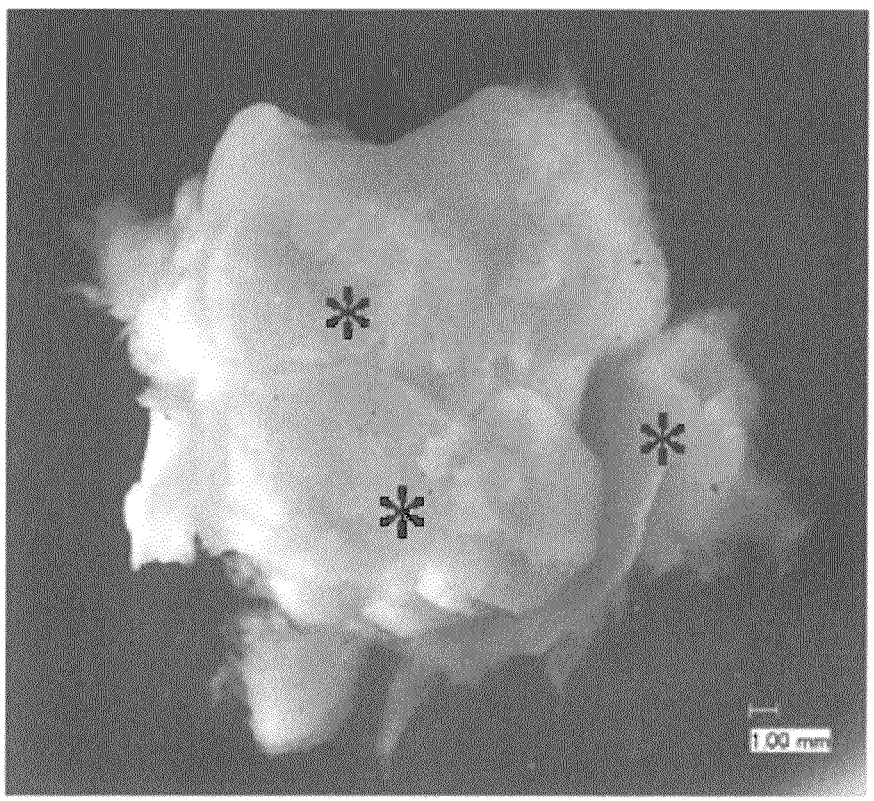
FIG. 22 is an explanatory view (stereomicroscope image) of the tooth immediately after being taken from the culture core cultured for 24 weeks in Example 2.

Twenty-four weeks after the initiation of culturing, the tooth was taken from the culture core and examined for the formation of tooth roots. FIG. 22 is an explanatory view (stereomicroscope image) of the tooth immediately after being taken from the culture core. From FIG. 22, it was confirmed that tooth roots were mainly covered with soft tissue (indicated by symbol "*").

—Stereomicroscope Image—

Figure 23:
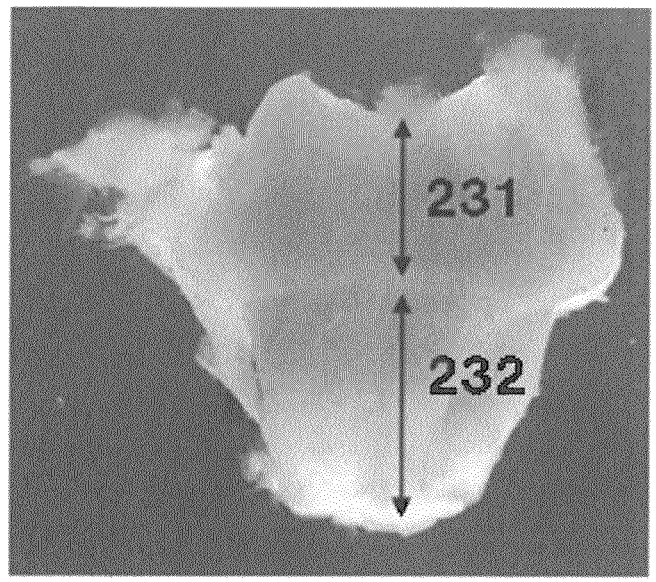
FIG. 23 is an explanatory view (stereomicroscope image) of the tooth cultured for 24 weeks in Example 2.
Figure 24:
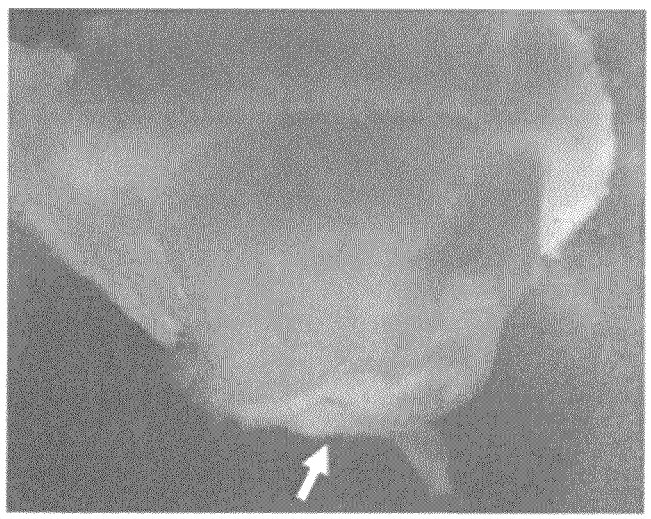
FIG. 24 is a stereomicroscope image obtained by photographing the 24-week-cultured tooth in an oblique direction with respect to the apex in Example 2.
Figure 25:
FIG. 25 is a stereomicroscope image obtained by photographing the 24-week-cultured tooth from the apex in Example 2.

The above-taken tooth was photographed with a stereomicroscope. Notably, upon photographing, the soft tissue was easily peeled off with tweezers and the elongated tooth root was exposed. FIG. 23 is an explanatory view (stereomicroscope image) of the tooth cultured for 24 weeks. From FIG. 23, it was confirmed that the new tooth root 232 was formed from the tooth crown 231. FIG. 24 is a stereomicroscope image obtained by photographing the 24-week-cultured tooth in an oblique direction with respect to the apex. FIG. 25 is a stereomicroscope image obtained by photographing the 24-week-cultured tooth from the apex. In FIGS. 24 and 25, each arrow indicates apical dental pulp. As shown in FIGS. 23 to 25, it was confirmed that the tooth root was formed.

—Soft X-ray Image—

Figure 26:
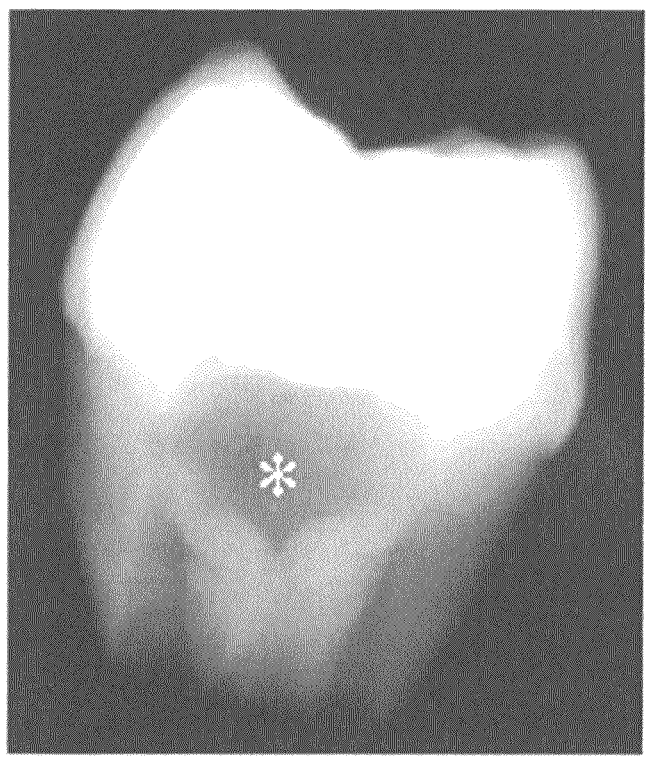
FIG. 26 is a soft X-ray image of the tooth cultured for 24 weeks in Example 2.

FIG. 26 is a soft X-ray image of the tooth cultured for 24 weeks. As shown in FIG. 26, it was confirmed that a dental pulp cavity (indicated by symbol "*") was formed.

—Micro-CT Image—

Figure 27A:
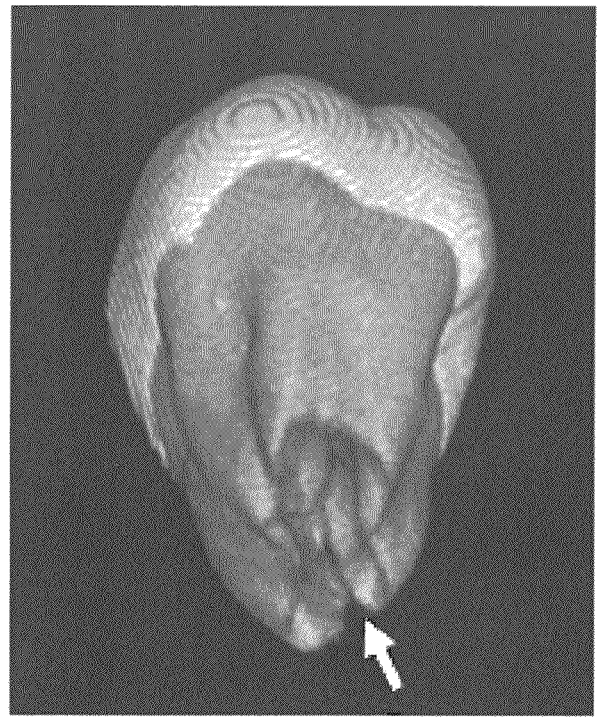
FIG. 27A is a micro-CT image of the side view of the tooth cultured for 24 weeks in Example 2.
Figure 27B:
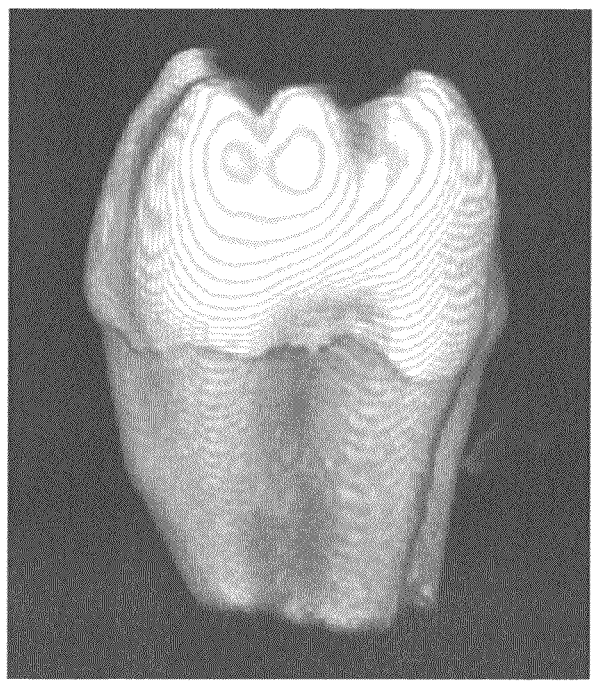
FIG. 27B is a micro-CT image of the side of the tooth cultured for 24 weeks in Example 2.
Figure 27C:
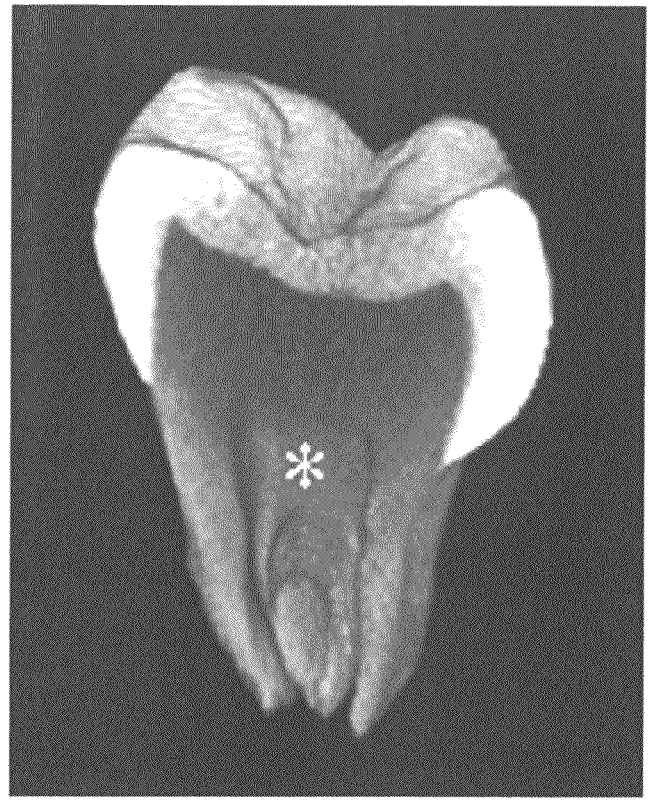
FIG. 27C is a micro-CT image of the cross-sectional side surface of the tooth cultured for 24 weeks in Example 2.
Figure 28A:
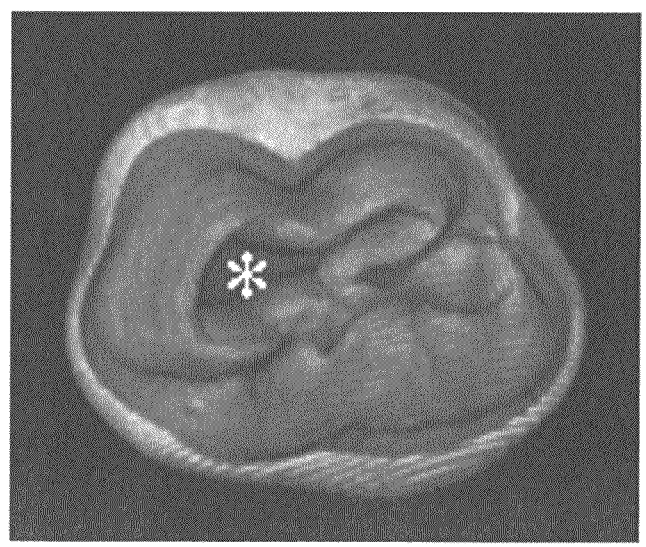
FIG. 28A is a micro-CT image of the tooth root from the apex, obtained by photographing a 24-week-cultured tooth from the apex in Example 2.
Figure 28B:
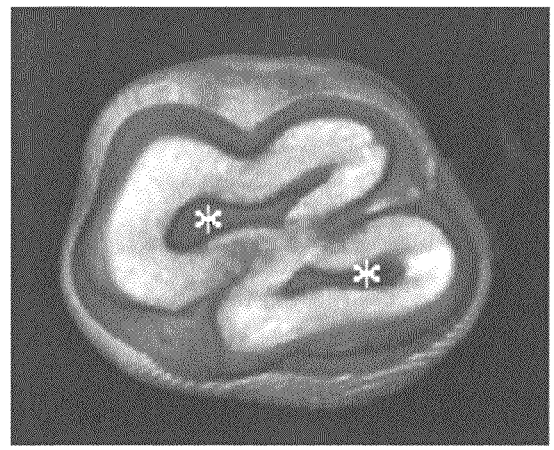
FIG. 28B is a micro-CT image of the cross-sectional surface of the tooth root, obtained by photographing a 24-week-cultured tooth from the apex in Example 2.
Figure 28C:
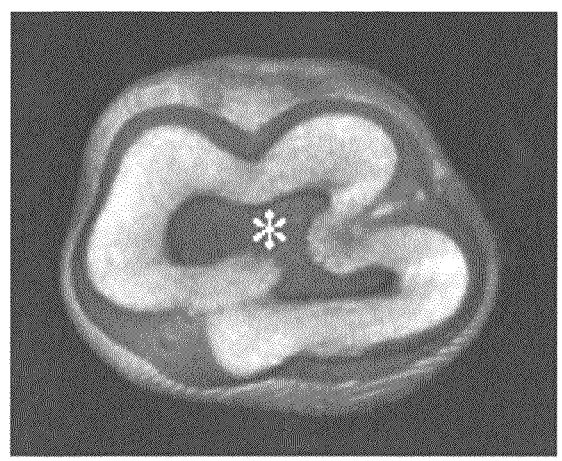
FIG. 28C is a micro-CT image of the cross-sectional surface of the cultured tooth root, obtained by photographing a 24-week-cultured tooth from the apex in Example 2.

FIGS. 27A and 27B are micro-CT images of the side view of the tooth cultured for 24 weeks. FIG. 27C is a micro-CT image of the cross-sectional side surface of the tooth cultured for 24 weeks. FIGS. 28A, 28B and 28C are micro-CT images of the cross-sectional surface of the tooth root, obtained by photographing the 24-week-cultured tooth from the apex. As shown in FIGS. 27A to 28C, it was confirmed that the tooth root was formed. In these figures, each arrow indicates apical dental pulp and the symbol "*" indicates dental pulp cavity.

—Analysis of Soft Tissue—

Analysis was performed on the soft tissue (indicated by symbol "*" in FIG. 22) with which the 24-week-cultured tooth had been covered.

Figure 29:
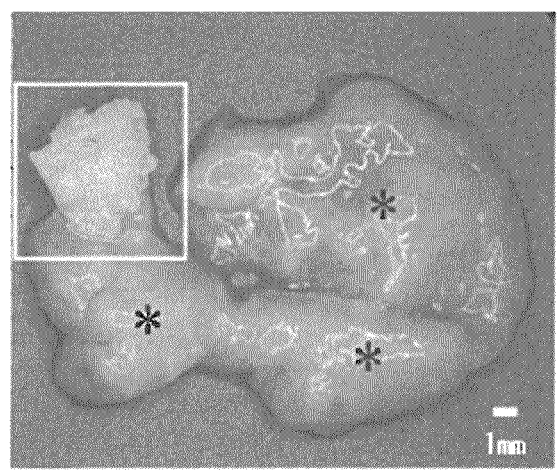
FIG. 29 is a stereomicroscope image of soft tissue peeled off from the cultured tooth in Example 2.

FIG. 29 is a stereomicroscope image of the soft tissue peeled off from the cultured tooth. The regions indicated by symbol "*" in FIG. 29 correspond to those indicated by symbol "*" in FIG. 22.

Figure 30:
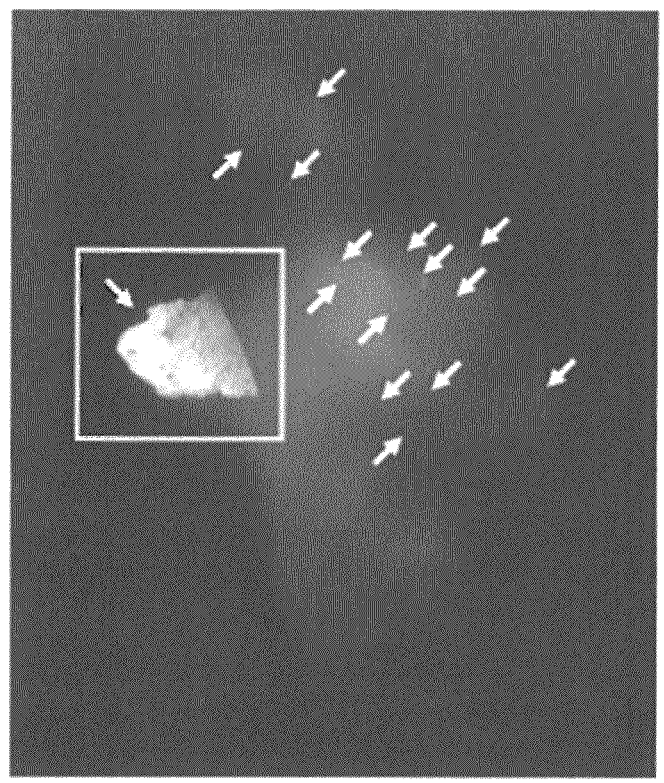
FIG. 30 is a soft X-ray image of soft tissue peeled off from the cultured tooth in Example 2.

FIG. 30 is a soft X-ray image of the soft tissue peeled off from the tooth. The boxed region in FIG. 30 corresponds to that in FIG. 29 and indicates large alveolar bone. Each arrow indicates a small mass of alveolar bone.

Figure 31A:
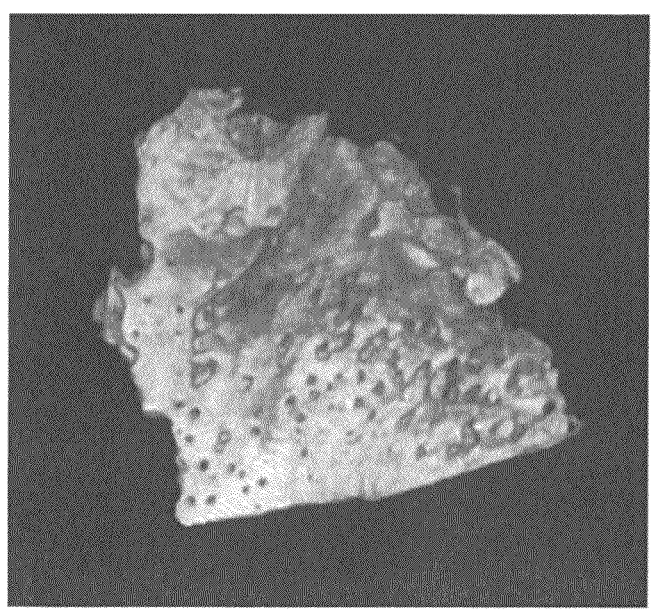
FIG. 31A is a micro-CT image of the boxed region of FIG. 30.
Figure 31B:
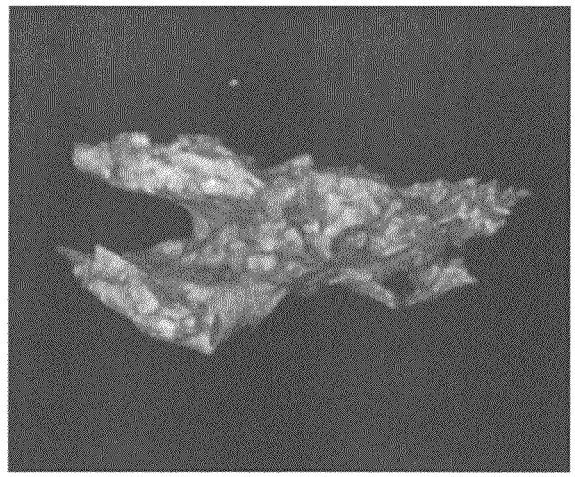
FIG. 31B is a micro-CT image of the boxed region of FIG. 30.

FIGS. 31A and 31B are micro-CT images of the large alveolar bone present in the boxed region of FIG. 30.

As a result of the analysis, it was confirmed that connective tissue and alveolar bone were formed.

Example 3

(Formation of Tooth Root and Periodontal Tissue Using Mouse Tooth Crown and Bone Marrow-derived Cell Sheet)

The procedure of Example 1 was repeated, except that a bone marrow-derived cell sheet was used instead of the periodontal ligament-derived cell sheet, to thereby form a tooth root, periodontal tissue, or a complex structure thereof.

—Preparation of Bone Marrow-derived Cell Sheet—

Extra bone marrow remaining after bone marrow transfusion was obtained. The thus-obtained bone marrow was cultured in a basal medium (DMEM/F12 (product of Invitrogen Co.)+15% FBS (product of Moregate BioTech Co., Lot No. 24300113)+1% non-essential amino acid liquid (product of Invitrogen Co.)+50 U/mL Penicillin (product of Invitrogen Co.)+50 µg/mL Streptomycin (product of Invitrogen Co.)+ 0.25 µg Fungizone (product of Invitrogen Co.)) for primary culture. When the medium was changed a few days after the initiation of culturing, adherent cells appeared on the culture dish while non-adherent (floating) cells were removed. The adherent cells were further cultured and, after reached confluency, the cells were dispensed into three culture dishes, where the bone marrow-derived cells were subcultured (passage 1). After reached confluency, the subcultured cells (passage 1) in each culture dish were further dispensed into three petri dishes, where the bone marrow-derived cells were subcultured (passage 2). After the bone marrow-derived cells (passage 2) had reached confluency, sheets formed of the bone marrow-derived cells were used as bone marrow-derived cell sheets.

—Four Weeks After Culturing—

Figure 32:
FIG. 32 is an explanatory view (stereomicroscope image) of the mouse tooth crown cultured for four weeks in Example 3.

Four weeks after the initiation of culturing, the tooth was taken out and examined for the formation of tooth root and periodontal tissue. FIG. 32 is an explanatory view (stereomicroscope image) of the mouse tooth crown cultured for four weeks.

As shown in FIG. 32, it was confirmed that alveolar bone was formed in part corresponding to the tooth roots.

—Soft X-ray Image—

Figure 33:
FIG. 33 is a soft X-ray image of the tooth cultured for four weeks in Example 3.

FIG. 33 is a soft X-ray image of the tooth cultured for four weeks. As shown in FIG. 33, alveolar bone was formed in addition to the tooth roots. And, it was also confirmed that a periodontal ligament space was formed between the tooth roots and the alveolar bone.

Example 4

(Formation of Tooth Root and Periodontal Tissue Using Mouse Tooth Crown and Dental Follicle-derived Cell Sheet)

The procedure of Example 1 was repeated, except that a dental follicle-derived cell sheet was used instead of the periodontal ligament-derived cell sheet, to thereby form a tooth root, periodontal tissue or a complex structure thereof.

—Preparation of Dental Follicle-derived Cell Sheet—

Soft tissue adhering around an incomplete human tooth which had been extracted was harvested (this soft tissue is called dental follicle, which is fibrillar connective tissue present around an incomplete tooth) and finely cut with a razor blade. The thus-obtained dental follicle tissue fragments were added to 0.1% trypsin-0.02% EDTA/PBS (−). The resultant mixture was heated at 37° C. for 30 min, and then strongly pipetted to separate dental follicle-derived cells. Subsequently, a liquid containing the dental follicle-derived cells was centrifugated at 300×g for 5 min. After removal of the supernatant through aspiration, a basal medium (DMEM/ F12 (product of Invitrogen Co.)+15% FBS (product of Moregate BioTech Co., Lot No. 24300113)+1% non-essential amino acid liquid (product of Invitrogen Co.)+50 U/mL Penicillin (product of Invitrogen Co.)+50 µg/mL Streptomycin (product of Invitrogen Co.)+0.25 µg Fungizone (product of Invitrogen Co.)) was added to the precipitate, followed by primarily culturing in a culture dish. Alternatively, the tissue fragments, which had been finely cut with the razor blade, were primarily cultured in a culture dish containing the above basal medium. In each method, the primarily cultured cells, after reached confluency, were dispensed into three culture dishes, where the dental follicle-derived cells were subcultured (passage 1). After reached confluency, the subcultured cells (passage 1) in each culture dish were further dispensed into three culture dishes, where the dental follicle-derived cells were subcultured (passage 2). After the dental follicle-derived cells (passage 2) had reached confluency, sheets formed of the dental follicle-derived cells were used as dental follicle-derived cell sheets.

—Four Weeks After Culturing—

Figure 34:
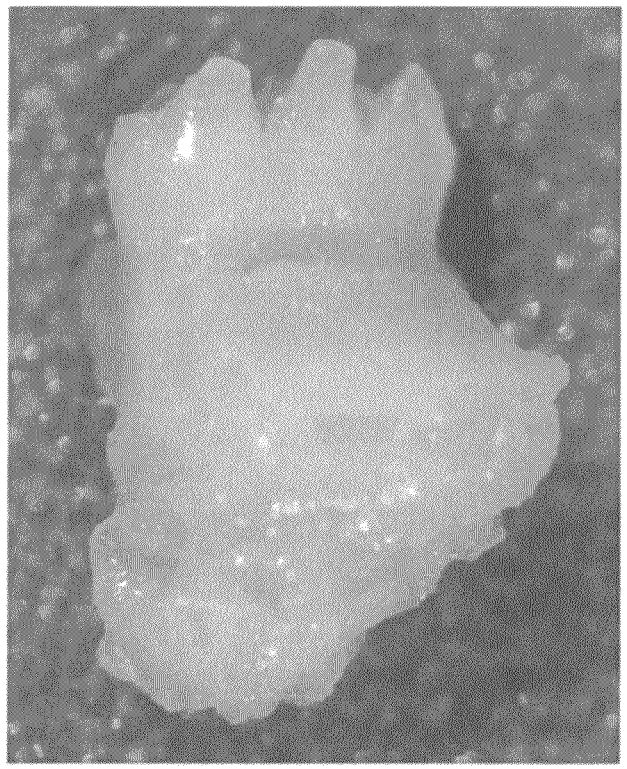
FIG. 34 is an explanatory view (stereomicroscope image) of the mouse tooth crown cultured for four weeks in Example 4.

Four weeks after the initiation of culturing, the tooth was taken out and examined for the formation of tooth roots and periodontal tissue. FIG. 34 is an explanatory view (stereomicroscope image) of the mouse tooth crown cultured for four weeks.

As shown in FIG. 34, it was confirmed that alveolar bone was formed in part corresponding to the tooth roots.

—Soft X-ray Image—

Figure 35:
FIG. 35 is a soft X-ray image of the tooth cultured for four weeks in Example 4.

FIG. 35 is a soft X-ray image of the tooth cultured for four weeks. As shown in FIG. 35, alveolar bone was formed in addition to the tooth roots. And, it was also confirmed that a periodontal ligament space was formed between the tooth roots and the alveolar bone.

Example 5

(Formation of Tooth Root and Periodontal Tissue Using Mouse Tooth Crown and Dental Pulp-derived Cell Sheet)

The procedure of Example 1 was repeated, except that a dental pulp-derived cell sheet was used instead of the periodontal ligament-derived cell sheet, to thereby form a tooth root, periodontal tissue or a complex structure thereof.

—Preparation of Dental Pulp-derived Cell Sheet—

An extracted human tooth was cut with a dental steel bar at the cervical region of the tooth (i.e., the boundary region between enamel and cementum) while cooled with Flanks solution (product of NISSUI Co.). Then, dental pulp tissue was taken from the dental pulp cavities of tooth crown and tooth root, and was finely cut with a razor blade. The thus-obtained dental pulp tissue was added to 0.1% trypsin-0.02% EDTA/PBS (−). The resultant mixture was heated at 37° C. for 30 min, and then strongly pipetted to separate dental pulp-derived cells. Subsequently, a liquid containing the dental pulp-derived cells was centrifugated at 300×g for 5 min. After removal of the supernatant through aspiration, a basal medium (DMEM/F12 (product of Invitrogen Co.)+15% FBS (product of Moregate BioTech Co., Lot No. 24300113)+1% non-essential amino acid liquid (product of Invitrogen Co.)+ 50 U/mL Penicillin (product of Invitrogen Co.)+50 μg/mL Streptomycin (product of Invitrogen Co.)+0.25 μg Fungizone (product of Invitrogen Co.)) was added to the precipitate, followed by primarily culturing in a culture dish. Alternatively, the tissue fragments, which had been finely cut with the razor blade, were primarily cultured in a culture dish containing the above basal medium. In each method, the primarily cultured cells, after reached confluency, were dispensed into three culture dishes, where the dental pulp-derived cells were subcultured (passage 1). After reached confluency, the subcultured cells (passage 1) in each culture dish were further dispensed into three culture dishes, where the dental pulp-derived cells were subcultured (passage 2). After the dental pulp-derived cells (passage 2) had reached confluency, sheets formed of the dental pulp-derived cells were used as dental pulp-derived cell sheets.

—Four Weeks After Culturing—

Figure 36:
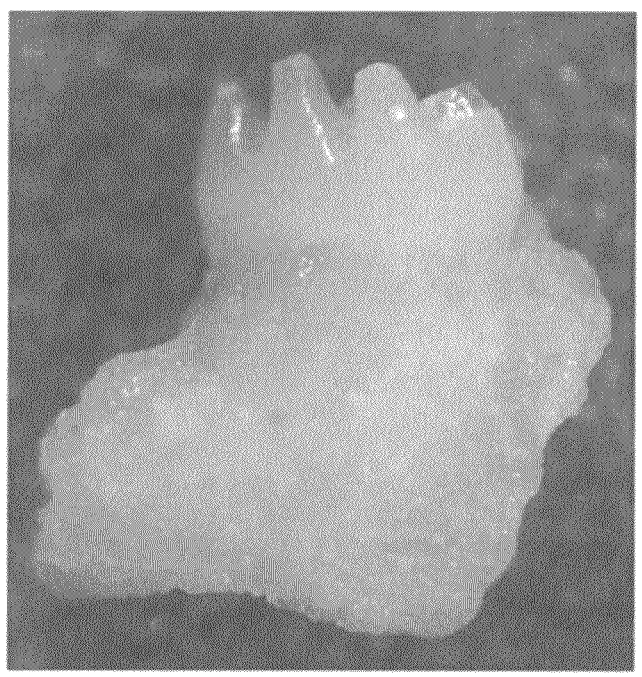
FIG. 36 is an explanatory view (stereomicroscope image) of the mouse tooth crown cultured for four weeks in Example 5.

Four weeks after the initiation of culturing, the tooth was taken out and examined for the formation of tooth root and periodontal tissue. FIG. 36 is an explanatory view (stereomicroscope image) of the mouse tooth crown cultured for four weeks.

As shown in FIG. 36, it was confirmed that alveolar bone was formed in part corresponding to the tooth roots.

—Soft X-ray Image—

Figure 37:
FIG. 37 is a soft X-ray image of the tooth cultured for four weeks in Example 5.

FIG. 37 is a soft X-ray image of the tooth cultured for four weeks. As shown in FIG. 37, alveolar bone was formed in addition to the tooth roots. And, it was also confirmed that a periodontal ligament space was formed between the tooth roots and the alveolar bone.

Example 6

(Formation of Tooth Root and Periodontal Tissue Using Mouse Tooth Crown and Dental Papilla-derived Cell Sheet)

The procedure of Example 1 was repeated, except that a dental papilla-derived cell sheet was used instead of the periodontal ligament-derived cell sheet, to thereby form a tooth root, periodontal tissue or a complex structure thereof.

—Preparation of Dental Papilla-derived Cell Sheet—

Using a human extracted tooth with an incomplete tooth root, dental pulp tissue located at the apex of tooth root (this dental pulp tissue is called dental papilla or root apical papilla) was taken and finely cut with a razor blade. The thus-obtained dental papilla tissue fragments were added to 0.1% trypsin-0.02% EDTA/PBS (−). The resultant mixture was heated at 37° C. for 30 min, and then strongly pipetted to separate dental papilla-derived cells. Subsequently, a liquid containing the dental papilla-derived cells was centrifugated at 300×g for 5 min. After removal of the supernatant through aspiration, a basal medium (DMEM/F12 (product of Invitrogen Co.)+15% FBS (product of Moregate BioTech Co., Lot No. 24300113)+1% non-essential amino acid liquid (product of Invitrogen Co.)+50 U/mL Penicillin (product of Invitrogen Co.)+50 μg/mL Streptomycin (product of Invitrogen Co.)+0.25 μg Fungizone (product of Invitrogen Co.)) was added to the precipitate, followed by primarily culturing in a culture dish. Alternatively, the tissue fragments, which had been finely cut with the razor blade, were primarily cultured in a culture dish containing the above basal medium. In each method, the primarily cultured cells, after reached confluency, were dispensed into three petri dishes, where the dental papilla-derived cells were subcultured (passage 1). After reached confluency, the subcultured cells (passage 1) in each culture dish were further dispensed into three culture dishes, where the dental papilla-derived cells were subcultured (passage 2). After the dental papilla-derived cells (passage 2) had reached confluency, sheets formed of the dental papilla-derived cells were used as dental papilla-derived cell sheets.

—Four Weeks After Culturing—

Figure 38:
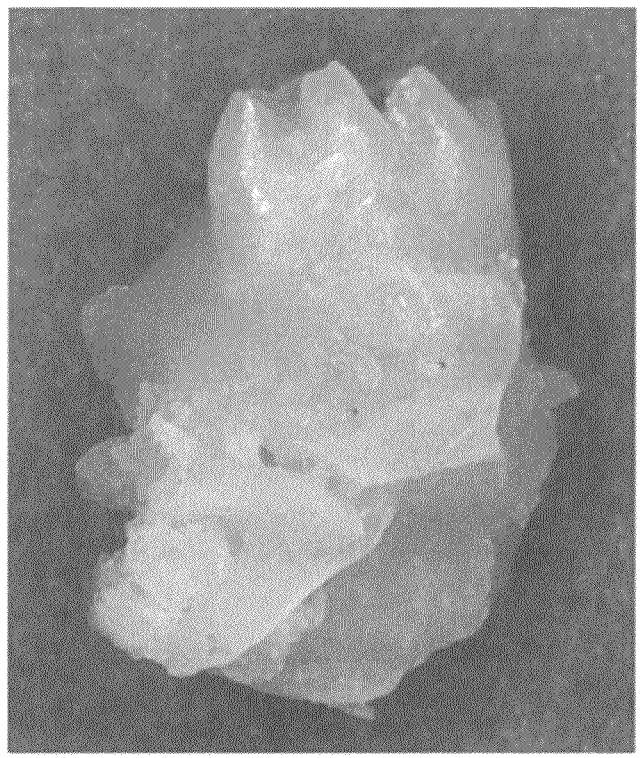
FIG. 38 is an explanatory view (stereomicroscope image) of the mouse tooth crown cultured for four weeks in Example 6.

Four weeks after the initiation of culturing, the tooth was taken out and examined for the formation of tooth root and periodontal tissue. FIG. 38 is an explanatory view (stereomicroscope image) of the mouse tooth crown cultured for four weeks.

As shown in FIG. 38, it was confirmed that alveolar bone was formed in part corresponding to the tooth roots.

—Soft X-ray Image—

Figure 39:
FIG. 39 is a soft X-ray image of the tooth cultured for four weeks in Example 6.

FIG. 39 is a soft X-ray image of the tooth cultured for four weeks. As shown in FIG. 39, alveolar bone was formed in addition to the tooth roots. And, it was also confirmed that a periodontal ligament space was formed between the tooth roots and the alveolar bone.

Example 7

(Formation of Tooth Root and Periodontal Tissue Using Mouse Tooth Crown and Periodontal Ligament-derived Cell-Containing Porous Base Material)

<Formation of Culture Core>

—Preparation of Tooth Crown—

A mouse tooth crown was provided in the same manner as in Example 1.

—Preparation of Periodontal Ligament-Derived Cells—

The periodontal ligament tissue was separated from the surface of the tooth root of an extracted tooth of adult human with a single-edged razor blade, to thereby obtain fragments of the tissue. The thus-taken periodontal ligament tissue fragments were further cut with a razor blade and added to 0.1% trypsin-0.02% EDTA/PBS (−). The resultant mixture was heated at 37° C. for 30 min, and then strongly pipetted to separate periodontal ligament-derived cells. Subsequently, a liquid containing the periodontal ligament-derived cells was centrifugated at 300×g for 5 min. After removal of the supernatant through aspiration, a basal medium (DMEM/F12 (product of Invitrogen Co.)+15% FBS (product of Moregate BioTech Co., Lot No. 24300113)+1% non-essential amino acid liquid (product of Invitrogen Co.)+50 U/mL Penicillin (product of Invitrogen Co.)+50 μg/mL Streptomycin (product of Invitrogen Co.)+0.25 μg Fungizone (product of Invitrogen Co.)) was added to the precipitate, followed by primarily culturing in a culture dish, to thereby prepare periodontal ligament-derived cells.

—Preparation of Periodontal Ligament-Derived Cell-containing Porous Base Material—

The porous base material used was TERDERMIS (registered trademark) (product of Olympus Terumo Biomaterials Corp.). The porous base material (in the form of sheet with a size of 4 cm×4 cm) was impregnated with the above basal medium. Then, the periodontal ligament-derived cells ($2 \times 10^7$ cells/mL) were seeded in the porous base material, followed by culturing at 37° C. for 72 hours, to thereby prepare a periodontal ligament-derived cell-containing porous base material.

—Culture Core—

The mouse tooth crown was wrapped with and embedded in the above periodontal ligament-derived cell-containing porous base material, to thereby obtain a culture core.

<Formation of Tooth Root and Periodontal Tissue>

The above culture core was cultured in the following medium: 15% FBS-containing DMEM/F12 medium containing natural ETFs at 0.1 mL/mL. The medium was changed every a few days. Notably, the natural ETFs were prepared in the same manner as in Example 1.

—Four Weeks After Culturing—

Figure 40:
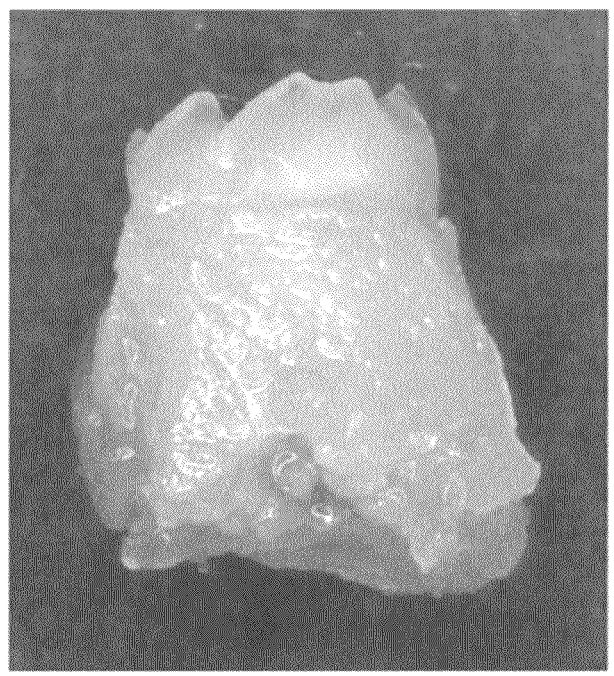
FIG. 40 is an explanatory view (stereomicroscope image) of the mouse tooth crown cultured for four weeks in Example 7.

Four weeks after the initiation of culturing, the tooth was taken out and examined for the formation of tooth root and periodontal tissue. FIG. 40 is an explanatory view (stereomicroscope image) of the mouse tooth crown cultured for four weeks.

As shown in FIG. 40, it was confirmed that alveolar bone was formed in part corresponding to the tooth roots.

—Soft X-ray Image—

Figure 41:
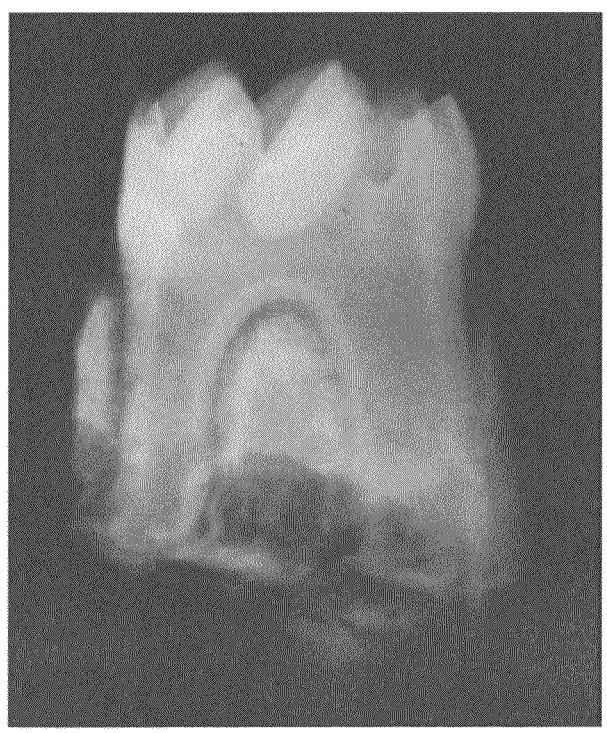
FIG. 41 is a soft X-ray image of the tooth cultured for four weeks in Example 7.

FIG. 41 is a soft X-ray image of the tooth cultured for four weeks. As shown in FIG. 41, alveolar bone was formed in addition to the tooth roots. And, it was also confirmed that a periodontal ligament space was formed between the tooth roots and the alveolar bone.

Example 8

(Formation of Tooth Root and Periodontal Tissue Using Mouse Tooth Crown, Periodontal Ligament-derived Cell Sheet and Periodontal Ligament-derived Cell-dontaining Porous Base Material)

<Formation of Culture Core>

—Preparation of Tooth Crown—

A mouse tooth crown was provided in the same manner as in Example 1.

—Preparation of Periodontal Ligament-derived Cell Sheet—

A periodontal ligament-derived cell sheet was prepared in the same manner as in Example 1.

—Pre-culturing—

Pre-culturing was performed in the same manner as in Example 1, whereby the mouse tooth crown was fixed on the human periodontal ligament-derived cell sheet.

—Preparation of Periodontal Ligament-derived Cell-containing Porous Base Material—

A periodontal ligament-derived cell-containing porous base material was prepared in the same manner as in Example 4.

—Culture Core—

The procedure of Example 1 was repeated, except that TERDERMIS (cell-free) was changed to the above periodontal ligament-derived cell-containing porous base material and that the mouse tooth crown was embedded in the human periodontal ligament-derived cell sheet and the periodontal ligament-derived cell-containing porous base material, to thereby obtain a culture core.

<Formation of Tooth Root and Periodontal Tissue>

The above culture core was cultured in the following medium: 15% FBS-containing DMEM/F12 medium containing natural ETFs at 0.1 mL/mL. The medium was changed every a few days. Notably, the natural ETFs were prepared in the same manner as in Example 1.

—Four Weeks After Culturing—

Figure 42:
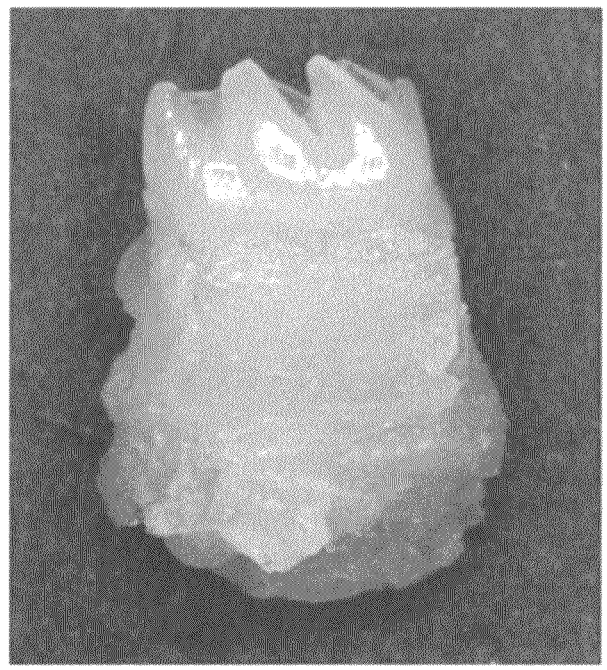
FIG. 42 is an explanatory view (stereomicroscope image) of the mouse tooth crown cultured for four weeks in Example 8.

Four weeks after the initiation of culturing, the tooth was taken out and examined for the formation of tooth root and periodontal tissue. FIG. 42 is an explanatory view (stereomicroscope image) of the mouse tooth crown cultured for four weeks.

As shown in FIG. 42, it was confirmed that alveolar bone was formed in part corresponding to the tooth roots.

—Soft X-ray Image—

Figure 43:
FIG. 43 is a soft X-ray image of the tooth cultured for four weeks in Example 8.

FIG. 43 is a soft X-ray image of the tooth cultured for four weeks. As shown in FIG. 43, alveolar bone was formed in addition to the tooth roots. And, it was also confirmed that a periodontal ligament space was formed between the tooth roots and the alveolar bone.

Example 9

(Formation of Tooth Root and Periodontal Tissue Using Mouse Tooth Crown and Periodontal Ligament-derived Cell Sheet)

The procedure of Example 1 was repeated, except that the natural ETFs were changed to the following rhOEFs, to thereby form tooth root and periodontal tissue.

In the medium for the culture core, the amounts of the components of the rhOEFs are as follows:

IL-1β (trade name: IL-1β, product of Acris Antibodies): 150 pg/mL
IL-6 (trade name: IL-6, product of PeproTech): 100 pg/mL
IL-8 (trade name: IL-8, product of PeproTech): 1.0 ng/mL
IL-9 (trade name: IL-9, product of R&D systems) 450 pg/mL
EGF (trade name: EGF, product of Acris Antibodies): 1.5 ng/mL
IGF-I (trade name: IGF-I, product of Biomedical Technology): 20 ng/mL
GH (trade name: hGH, product of Novo Nordisk): 2.5 ng/mL
PDGF-AB (trade name: PDGF-AB, product of PeproTech): 0.6 ng/mL
VEGF (trade name: VEGF, product of Bachem Feinche-mikalien AG): 3.2 ng/mL
LIF (trade name: LIF, product of Chemicon International): 35 pg/mL
HGF (trade name: HGF, product of R&D systems): 1.0 ng/mL
FGF-2 (trade name: FGF-2, product of ProSpec-Tany Technogene): 20 ng/mL
FGF-1 (trade name: FGF-1, product of ProSpec-Tany Technogene): 5.0 ng/mL
BMP-2 (trade name: BMP-2, product of R&D systems): 10 ng/mL
BMP-4 (trade name: BMP-4, product of R&D systems): 15 ng/mL
M-CSF (trade name: M-CSF, product of R&D systems): 10 μg/mL
Dexamethasone (trade name: dexamethasone, product of BIOMOL International, LP): 5 μM
Insulin (trade name: insulin, product of Chemicon International): 7.5 ng/mL Thyroxine (trade name: thyroxine, product of SIGMA): 5.5 ng/mL Thyrocalcitonin (trade name: calcitonin (human), product of Biogenesis): 10 ng/mL Ascorbic acid (trade name: ascorbic acid, product of SIGMA): 50 μg/mL β-Glycerophosphate (trade name: β-glycerophosphate, product of SIGMA): 10 mM —Four Weeks After Culturing—

Figure 44:
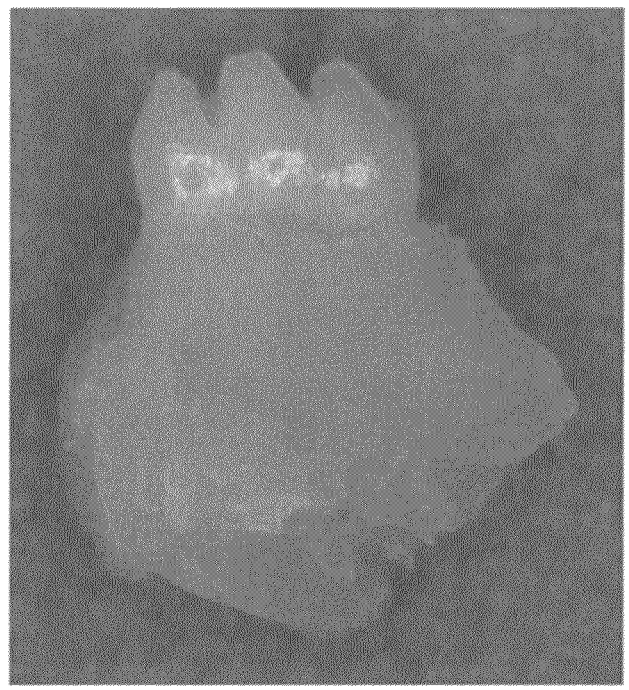
FIG. 44 is an explanatory view (stereomicroscope image) of the mouse tooth crown cultured for four weeks in Example 9.

Four weeks after the initiation of culturing, the tooth was taken out and examined for the formation of tooth root and periodontal tissue. FIG. 44 is an explanatory view (stereomicroscope image) of the mouse tooth crown cultured for four weeks.

As shown in FIG. 44, it was confirmed that alveolar bone was formed in part corresponding to the tooth roots.

—Soft X-ray Image—

Figure 45:
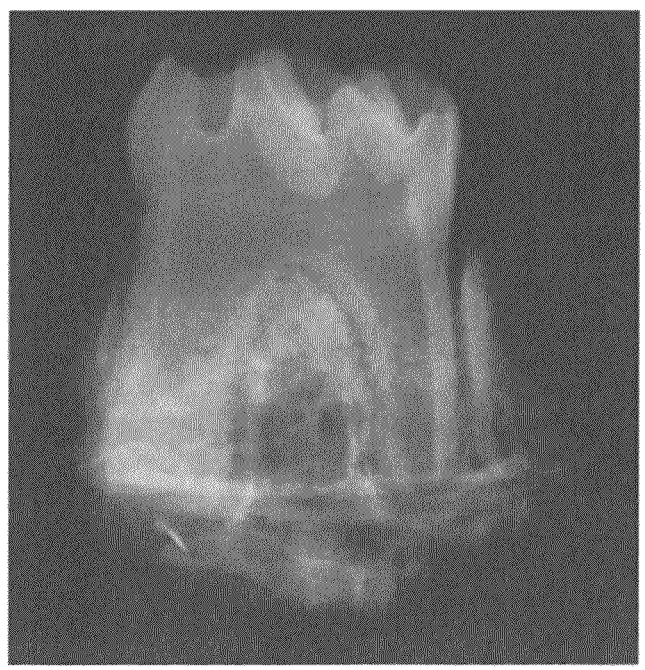
FIG. 45 is a soft X-ray image of the tooth cultured for four weeks in Example 9.

FIG. 45 is a soft X-ray image of the tooth cultured for four weeks. As shown in FIG. 45, alveolar bone was formed in addition to the tooth roots. And, it was also confirmed that a periodontal ligament space was formed between the tooth roots and the alveolar bone.

Example 10

(Formation of Tooth Root and Periodontal Tissue Using Mouse Tooth Crown and Periodontal Ligament-derived Cell Sheet)

The procedure of Example 7 was repeated, except that the natural ETFs were changed to the rhOEFs used in Example 9, to thereby form tooth roots and periodontal tissue.

—Four Weeks After Culturing—

Figure 46:
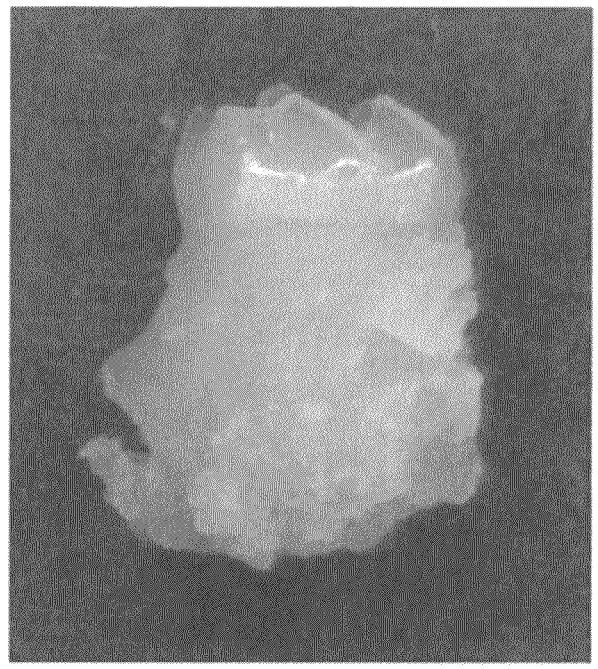
FIG. 46 is an explanatory view (stereomicroscope image) of the mouse tooth crown cultured for four weeks in Example 10.

Four weeks after the initiation of culturing, the tooth was taken out and examined for the formation of tooth root and periodontal tissue. FIG. 46 is an explanatory view (stereomicroscope image) of the mouse tooth crown cultured for four weeks.

As shown in FIG. 46, it was confirmed that alveolar bone was formed in part corresponding to the tooth roots.

—Soft X-ray Image—

Figure 47:
FIG. 47 is a soft X-ray image of the tooth cultured for four weeks in Example 10.

FIG. 47 is a soft X-ray image of the tooth cultured for four weeks. As shown in FIG. 47, alveolar bone was formed in addition to the tooth roots. And, it was also confirmed that a periodontal ligament space was formed between the tooth roots and the alveolar bone.

Example 11

(Formation of Tooth Root and Periodontal Tissue Using Mouse Tooth Crown and Periodontal Ligament-derived Cell Sheet)

The procedure of Example 8 was repeated, except that the natural ETFs were changed to the rhOEFs used in Example 9, to thereby form tooth root and periodontal tissue.

—Four Weeks After Culturing—

Figure 48:
FIG. 48 is an explanatory view (stereomicroscope image) of the mouse tooth crown cultured for four weeks in Example 11.

Four weeks after the initiation of culturing, the tooth was taken out and examined for the formation of tooth root and periodontal tissue. FIG. 48 is an explanatory view (stereomicroscope image) of the mouse tooth crown cultured for four weeks.

As shown in FIG. 48, it was confirmed that alveolar bone was formed in part corresponding to the tooth roots.

—Soft X-ray Image—

Figure 49:
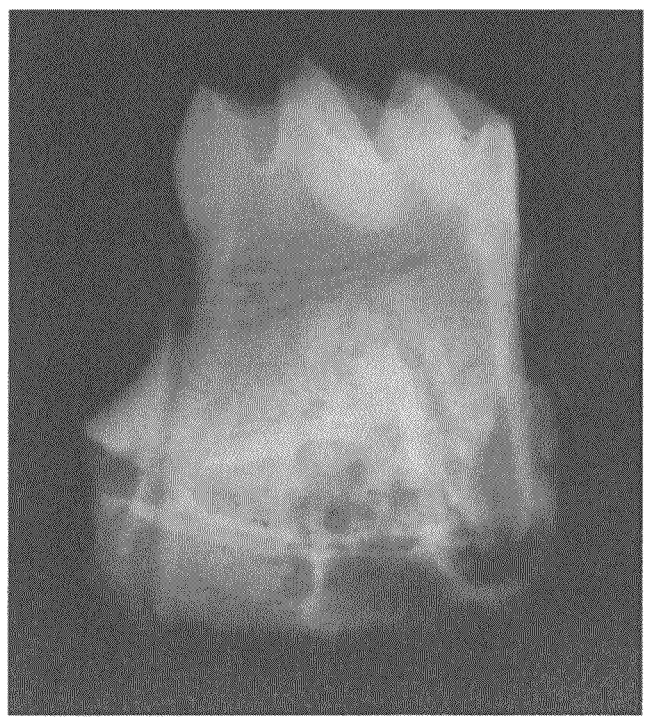
FIG. 49 is a soft X-ray image of the tooth cultured for four weeks in Example 11.

FIG. 49 is a soft X-ray image of the tooth cultured for four weeks. As shown in FIG. 49, alveolar bone was formed in addition to the tooth roots. And, it was also confirmed that a periodontal ligament space was formed between the tooth roots and the alveolar bone.

As described above, it was confirmed that a regenerated tooth containing a tooth root was formed by treating a mouse tooth crown or a human tooth crown through in vitro culture; i.e., without using xenotransplantation or allotransplantation (in vivo culture). In addition, it was also confirmed that the tooth root having periodontal tissues was formed, and as a result, a regenerated tooth having both the tooth and periodontal tissues was obtained. Notably, the technique of the present invention is thought to be applicable to in vitro formation of other tissues or organs in addition to teeth.

The method of the present invention can form a tooth root with periodontal tissues using in vitro culture; i.e., without using xenotransplantation or allotransplantation (in vivo culture), and thus can form a regenerated tooth involving no possibility of immune rejection and infection with, for example, viruses.

Also, the regenerated tooth of the present invention can be obtained by the method of the present invention. Thus, the regenerated tooth can be transplanted into the portion from which the tooth has been lost, and also can be suitably used for the cases involving loss of alveolar bone.

The present invention can be suitably applied to the regeneration of other tissues or organs in addition to teeth.

What is claimed is:

1. A method for forming at least a tooth root in a tooth containing a tooth crown, the method comprising:
   forming a culture core containing the tooth and a cell-containing base material, the tooth being wrapped with the cell-containing base material, and
   culturing the culture core in a medium so as to form at least the tooth root in the tooth contained in the culture core,
   wherein the cell-containing base material comprises at least one kind of cells selected from periodontal ligament-derived cells, bone marrow-derived cells, dental follicle-derived cells, dental pulp-derived cells and dental papilla-derived cells, and
   wherein the medium comprises at least one selected from the group consisting of the following (1) and (2):
      (1) a component contained in a conditioned medium of a serum-free-cultured cell line of a human uterocervical squamous carcinoma cell line; and
      (2) an additive;
   wherein the component in (1) comprises IL-1α, IL-1β, IL-2, IL-3, IL-4, IL-5, IL-6, IL-9, IL-10, IL-12, EGF, TNF-α, TGF-α, IGF-I, GH, PDGF-AB, IGF-BP-3, FGF-2, VEGF, LIF, and HGF, and
   wherein the additive in (2) comprises IL-1β, IL-6, IL-8, IL-9, EGF, IGF-I, GH, PDGF-AB, VEGF, LIF, HGF, FGF-2, FGF-1, BMP-2, BMP-4, M-CSF, dexamethasone, insulin, thyroxine, thyrocalcitonin, ascorbic acid and β-glycerophosphate.

2. The method according to claim 1, wherein the culturing further provides a formation of periodontal tissue (periodontium).

3. The method according to claim 2, wherein the cell-containing base material is at least one of a cell sheet and a cell-containing porous base material.

4. The method according to claim 3, wherein the forming comprises pre-culturing the tooth on the cell sheet.

5. The method according to claim 3, wherein the culture core is wrapped with a cell-free porous base material.

6. The method according to claim 5, wherein the forming comprises pre-culturing the tooth on the cell sheet.

7. The method according to claim 2, wherein the culture core is wrapped with a cell-free porous base material.

8. The method according to claim 1, wherein the cell containing base material is at least one of a cell sheet and a cell-containing porous base material.

9. The method according to claim 8, wherein the culture core is wrapped with a cell-free porous base material.

10. The method according to claim 9, wherein the forming comprises pre-culturing the tooth on the cell sheet.

11. The method according to claim 8, wherein the forming comprises pre-culturing the tooth on the cell sheet.

12. The method according to claim 1, wherein the culture core is wrapped with a cell-free porous base material.

\* \* \* \* \*